US012807636B2

United States Patent

(12) United States Patent
Shibata et al.

(10) Patent No.: US 12,807,636 B2
(45) Date of Patent: Nov. 24, 2026

(54) COMPOUND OR SALT THEREOF, AND ANTITUMOR ACTIVATOR CONTAINING SAME AS ACTIVE INGREDIENT

(71) Applicants: AKITA UNIVERSITY, Akita (JP); TOHOKU UNIVERSITY, Sendai (JP)

(72) Inventors: Hiroyuki Shibata, Akita (JP); Yoshiharu Iwabuchi, Sendai (JP)

(73) Assignees: Akita University, Akita (JP); TOHOKU UNIVERSITY, Sendai (JP)

( * ) Notice: Subject to any disclaimer, the term of this patent is extended or adjusted under 35 U.S.C. 154(b) by 464 days.

(21) Appl. No.: 18/281,202

(22) PCT Filed: Feb. 25, 2022

(86) PCT No.: PCT/JP2022/008078
§ 371 (c)(1),
(2) Date: Sep. 8, 2023

(87) PCT Pub. No.: WO2022/190915
PCT Pub. Date: Sep. 15, 2022

(65) Prior Publication Data

US 2024/0158430 A1 May 16, 2024

(30) Foreign Application Priority Data

Mar. 10, 2021 (JP) ................................ 2021-038597

(51) Int. Cl.
*C07H 19/056* (2006.01)
*A61K 31/7056* (2006.01)
*A61P 35/00* (2006.01)

(52) U.S. Cl.
CPC ....... *C07H 19/056* (2013.01); *A61K 31/7056* (2013.01); *A61P 35/00* (2018.01)

(58) Field of Classification Search
CPC ..... C07H 19/056; C07H 15/203; A61P 35/00; A61K 31/7056
USPC ........................................................... 514/43
See application file for complete search history.

(56) References Cited

U.S. PATENT DOCUMENTS

2010/0152493 A1 6/2010 Shibata et al.

FOREIGN PATENT DOCUMENTS

JP 5050206 B2 10/2012

OTHER PUBLICATIONS

Kohyama et al, Org. Biomol. Chem. 2016, 14, 10683-106.*
Cagnoni et al, J. Org. Chem., 2011, 76, 3064-3077.*
International Search Report for PCT/JP2022/008078 dated May 10, 2022 [PCT/ISA/210].

* cited by examiner

*Primary Examiner* — Ganapathy Krishnan
(74) *Attorney, Agent, or Firm* — Sughrue Mion, PLLC

(57) ABSTRACT

Provided is a new compound or a salt thereof having improved in vivo efficacy and antitumor activity of a curcumin derivative, and an antitumor activator containing the new compound or the salt thereof as an active ingredient. The compound or a salt thereof is represented by the following general formula. $R^1$ to $R^4$ are substituents selected from a hydrogen atom, a $C_{1-4}$ lower alkyl group, a hydroxy $C_{1-4}$ lower alkyl group, a $C_{1-4}$ lower alkoxy $C_{1-4}$ lower alkyl group, and a $C_{1-4}$ lower alkoxy $C_{1-4}$ lower alkoxy $C_{1-4}$ lower alkyl group, and $R^1$ to $R^4$ may be the same or different. n is 1 to 6. Sugar is a monosaccharide or a disaccharide.

(I)

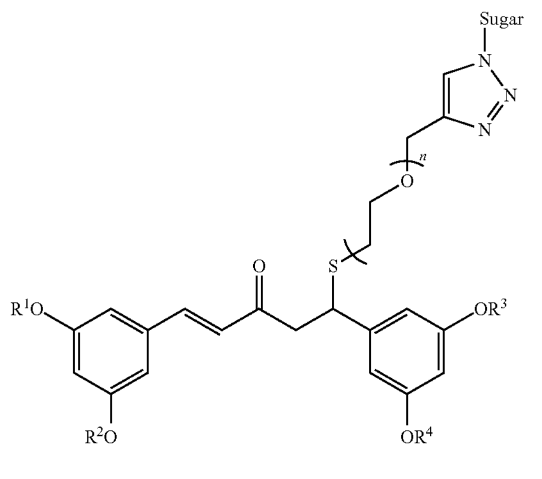

3 Claims, 19 Drawing Sheets

GO-Y190 (2.2 mg)

Chemical Formula:
$C_{33}H_{46}O_{15}S$
Molecular Weight:
714.7760
Clog P: 1.91

Turbidity: 0.22

GO-Y191 (2.1 mg)

Chemical Formula:
$C_{41}H_{62}O_{21}S_2$
Molecular Weight:
955.0460
Clog P: 0.37

Turbidity: not done

GO-Y192 (5.6 mg)

Chemical Formula:
$C_{36}H_{49}N_3O_{15}S$
Molecular Weight:
795.8540
Clog P: 1.20

Turbidity: 0.26

L-glucose
GO-Y197

Chemical Formula: $C_{42}H_{61}N_3O_{18}S$
Molecular Weight: 928.01

Turbidity: 0

D-mannose
GO-Y198
1.95 mg

Chemical Formula: $C_{42}H_{61}N_3O_{18}S$
Molecular Weight: 928.0130

Turbidity: 0

D-lactose
GO-Y199
7.3 mg

Chemical Formula: $C_{48}H_{71}N_3O_{23}S$
Molecular Weight: 1090.15400

Turbidity: 0.0014

D-maltose
GO-Y200
2.22 mg

Chemical Formula: $C_{48}H_{71}N_3O_{23}S$
Exact Mass: 1089.4199
Molecular Weight: 1090.1540

Turbidity: 0

GO-Y022

$C_{19}H_{18}O_5$
Exact Mass: 326.1154
Mol. Wt.: 326.3432
C, 69.93; H, 5.56; O, 24.51

Turbidity: 0.048

GO-Y136

Chemical Formula: $C_{28}H_{36}O_{11}S$
Exact Mass: 580.1978
Molecular Weight: 580.6438
Elemental Analysis: C, 57.92; H, 6.25; O, 30.31; S, 5.52

Turbidity: 0.083

GO-Y030

$C_{25}H_{30}O_9$
Exact Mass: 474.1890
Mol. Wt.: 474.5003
C, 63.28; H, 6.37; O, 30.35

Turbidity: 9.2 mf797

Chemical Formula: $C_{23}H_{35}N_3O_9S$
Molecular Weight: 529.60

β-deoxyglucose

GO-Y206 (31.0 mg)

Chemical Formula: $C_{42}H_{61}N_3O_{17}S$

Molecular Weight: 912.0140

IN VIVO GROWTH INHIBITORY EFFECT OF SOLUBILIZED GO-Y030 ON MALIGNANT MESOTHELIOMA

| | No tumors | Small disseminated masses | Large PC nodule |
|---|---|---|---|
| GO-Y199 | 1/5 (20%) | 4/5 (80%) | 1/5 (20%) (1 tumor, size 5 mm) |
| DMSO | 0/4 (0%) | 3/4 (75%) | 4/4 (100%) (1 tumor, 12 mm), (2 tumors, 10 mm, 13 mm), (2 tumors, 6 mm, 13 mm), (1 tumor, 7 mm) |

PATHOLOGICAL FINDINGS OF MALIGNANT MESOTHELIOMA TO WHICH SOLUBILIZED GO-Y030 WAS ADMINISTERED

COMPOUND OR SALT THEREOF, AND ANTITUMOR ACTIVATOR CONTAINING SAME AS ACTIVE INGREDIENT

CROSS REFERENCE TO RELATED APPLICATIONS

This application is a National Stage of International Application No. PCT/JP2022/008078 filed Feb. 25, 2022, claiming priority based on Japanese Patent Application No. 2021-038597 filed Mar. 10, 2021.

TECHNICAL FIELD

The present application relates to a novel compound or a salt thereof, and an antitumor activator containing the compound or the salt as an active ingredient.

BACKGROUND ART

Curcumin contained in spices or the like is known to have various pharmacological effects including an antitumor activity. For example, as the pharmacological effects of curcumin, antitumor activity, anti-inflammatory activity, anti-heart failure activity, antibacterial activity, radioprotective effect, and the like are known. It is also known that curcumin is an edible spice and has low toxicity.

The present inventors have previously disclosed a curcumin derivative having an enhanced antitumor activity while maintaining low toxicity in Patent Document 1. Specifically, Patent Document 1 discloses that a predetermined bis(arylmethylidene)acetone compound, which is a novel compound, or a salt thereof, and an expression inhibitor of Ki-Ras, ErbB2, c-Myc, or CyclinD1, a β-catenin decomposer, an expression enhancer of p53, an anticancer agent, or a carcinogenesis preventing agent, containing the compound or the salt as an active ingredient.

CITATION LIST

Patent Literature

Patent Document 1: JP 5050206 B

SUMMARY OF INVENTION

Technical Problem

As described in Patent Document 1, the present inventors have succeeded in developing a curcumin derivative having an enhanced antitumor activity of curcumin. However, the curcumin derivative of Patent Document 1 has low water solubility and cannot improve in vivo efficacy, which limits its pharmaceutical use.

In view of the above circumstances, an object of the present disclosure is to provide a novel compound or a salt thereof having improved in vivo efficacy and an antitumor activity of a curcumin derivative, and an antitumor activator containing the compound or the salt as an active ingredient.

Solution to Problem

The present disclosure provides a compound represented by the following general formula or a salt thereof as an aspect for solving the above issue:

Formula 1

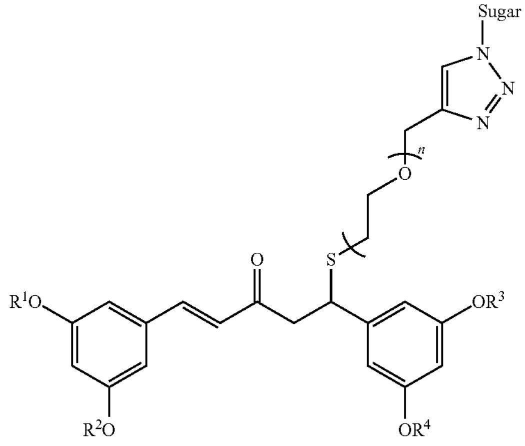

Herein, $R^1$ to $R^4$ are substituents selected from a hydrogen atom, a $C_{1-4}$ lower alkyl group, a hydroxy $C_{1-4}$ lower alkyl group, a $C_{1-4}$ lower alkoxy $C_{1-4}$ lower alkyl group, and a $C_{1-4}$ lower alkoxy $C_{1-4}$ lower alkoxy $C_{1-4}$ lower alkyl group. $R^1$ to $R^4$ may be the same or different from each other. n is 1 to 6. Sugar is a monosaccharide or a disaccharide.

The present disclosure also provides an antitumor activator containing the above compound or the salt thereof as an active ingredient. The antitumor activator may be an antitumor activator for gastric cancer, colorectal cancer, pancreatic cancer, malignant mesothelioma, or cutaneous T-cell lymphoma, an antitumor activator for pancreatic cancer, malignant mesothelioma, or cutaneous T-cell lymphoma, or an antitumor activator for pancreatic cancer.

Advantageous Effects of Invention

The compound or the salt thereof according to the present disclosure has improved water solubility as compared with the curcumin derivative of Patent Document 1, and thus has improved in vivo efficacy. Accordingly, it can be used for a wide range of pharmaceutical applications. In addition, the compound or the salt thereof according to the present disclosure has an improved antitumor activity as compared with the curcumin derivative of Patent Document 1. Furthermore, safety of the compound or the salt thereof according to the present disclosure has been confirmed in an experiment using mice.

DESCRIPTION OF EMBODIMENTS

Figure 1:
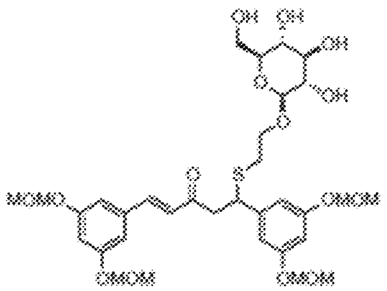
FIG. 1 indicates chemical structures of GO-Y190 to 192.
Figure 1:
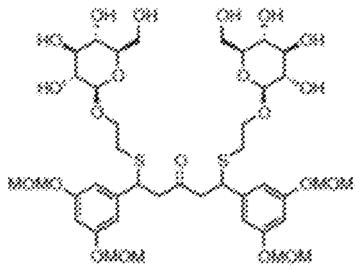
Figure 1:
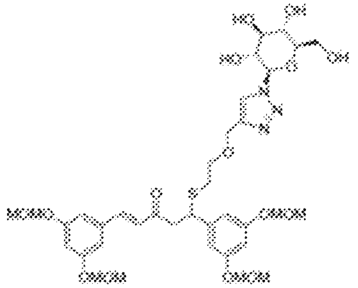
Figure 2:
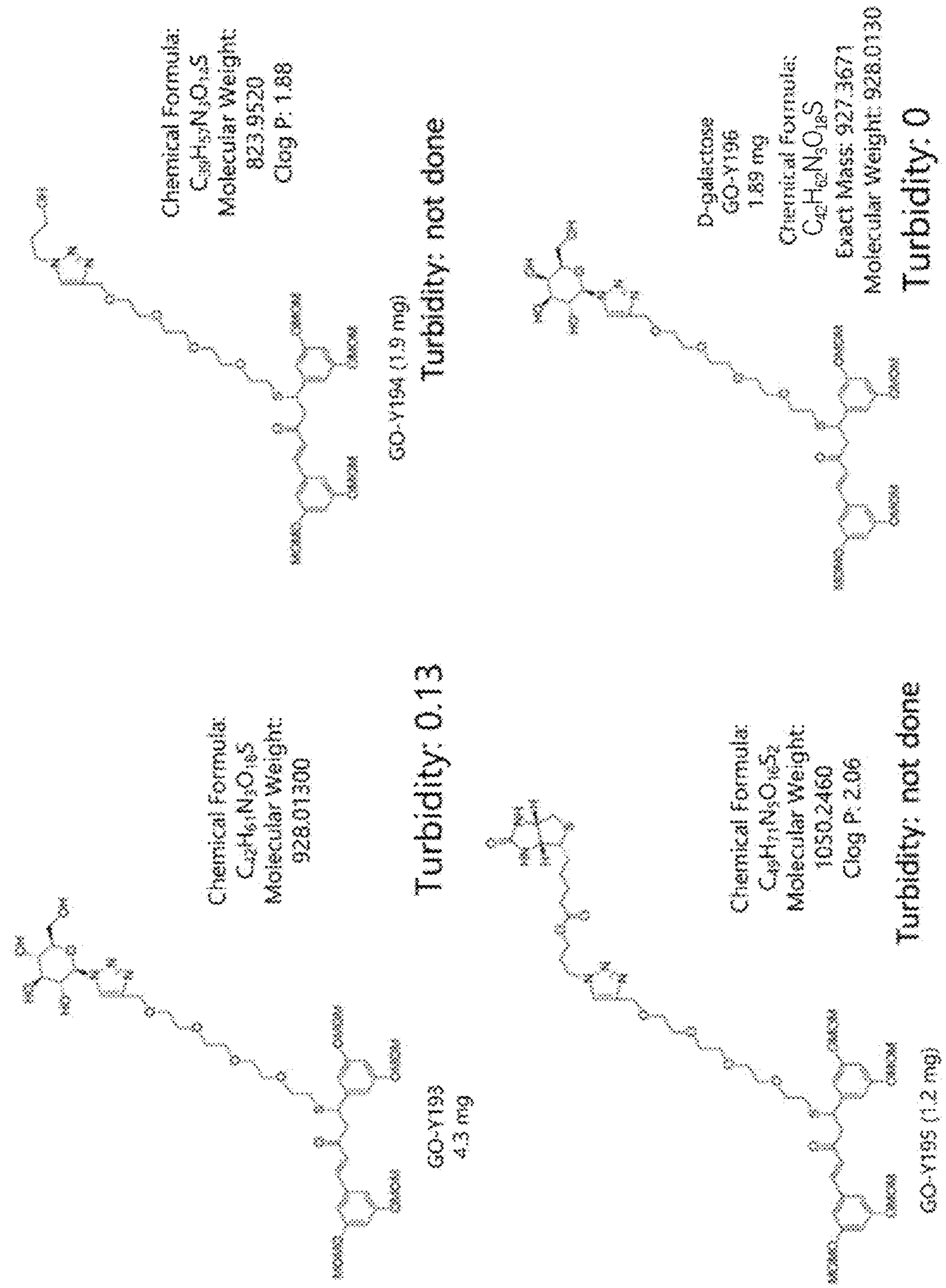
FIG. 2 indicates chemical structures of GO-Y193 to 196.
Figure 3:
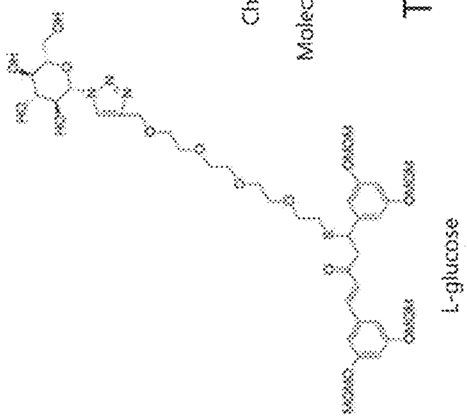
FIG. 3 indicates chemical structures of GO-Y197 to 200.
Figure 3:
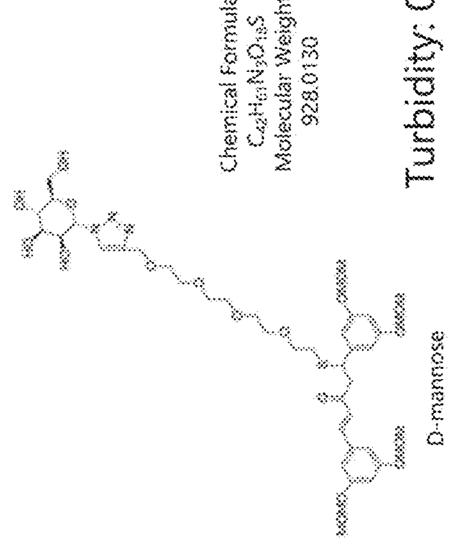
Figure 3:
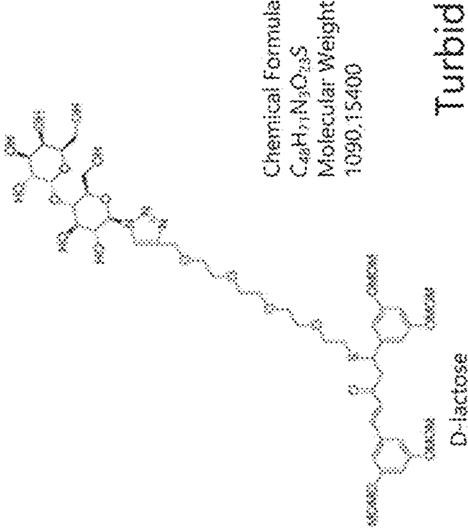
Figure 3:
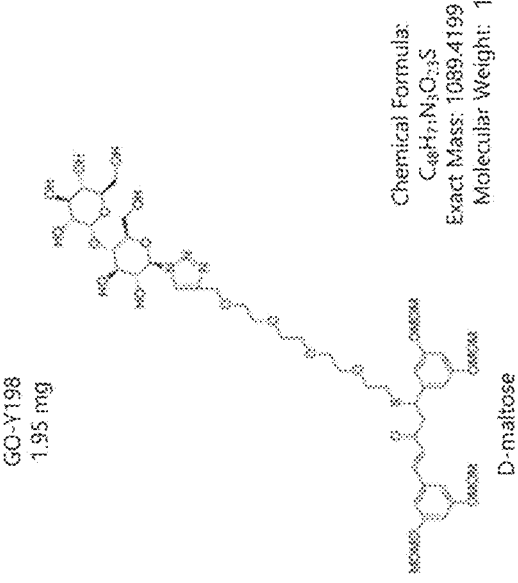
Figure 4:
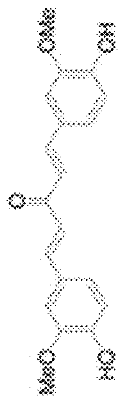
FIG. 4 indicates chemical structures of GO-Y022, GO-Y136, GO-Y030, and mf797.
Figure 4:
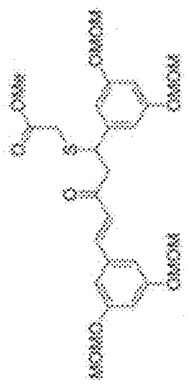
Figure 4:
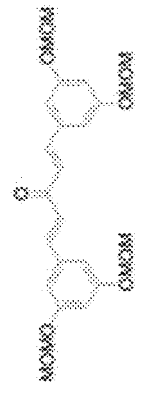
Figure 4:
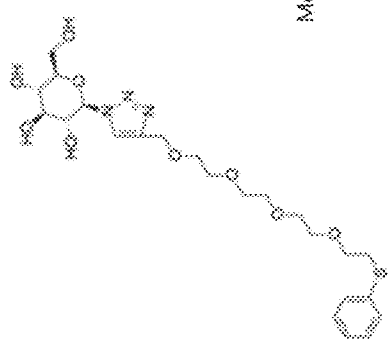
Figure 5:
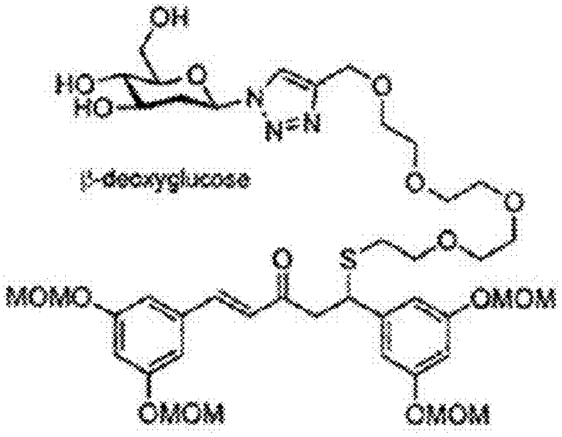
FIG. 5 indicates a chemical structure of GO-Y206.

The present inventors have conducted intensive studies to improve the in vivo efficacy (water solubility) of the curcumin derivative (diarylpentanoid derivative: DPA) of Patent Document 1. As a result, the present inventors have newly synthesized SuDPA in which a sugar (Sugar) is added to DPA via a linker. Then, as a result of various experiments conducted on the synthesized SuDPA, SuDPA has been remarkably improved in water solubility and antitumor activity as compared with DPA. In addition, SuDPA maintains the cancer molecule targeting property of DPA. Furthermore, it has been confirmed that SuDPA has low toxicity. On the basis of the above findings, the compound or the salt thereof according to the present disclosure has been invented. Hereinafter, the compound or the salt thereof according to the present disclosure will be described.

The present disclosure provides a compound represented by the following general formula or a salt thereof:

Formula 2

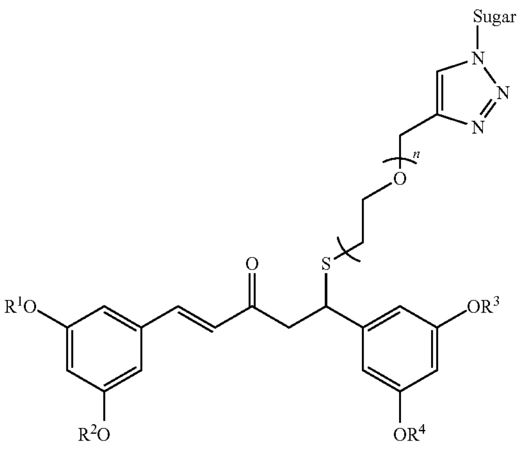

Herein, $R^1$ to $R^4$ are substituents selected from a hydrogen atom, a $C_{1-4}$ lower alkyl group, a hydroxy $C_{1-4}$ lower alkyl group, a $C_{1-4}$ lower alkoxy $C_{1-4}$ lower alkyl group, and a $C_{1-4}$ lower alkoxy $C_{1-4}$ lower alkoxy $C_{1-4}$ lower alkyl group. $R^1$ to $R^4$ may be the same or different from each other. $R^1$ to $R^4$ may be a $C_{1-4}$ lower alkoxy $C_{1-4}$ lower alkyl group or a methoxymethyl group.

Here, the $C_{1-4}$ carbon chain in the substituent described above may be a straight chain or a branched chain. The carbon chain may be substituted with a halogen atom or the like.

n that represents a length of a linker site (vinyl alcohol site) connecting a DPA site and a saccharide site is 1 to 6. From the viewpoint of improving water solubility, n may be 2 to 5, 3 to 4, or 4.

Sugar is a monosaccharide or a disaccharide, and deoxy sugars thereof are also included. Examples of the monosaccharide include glucose, galactose, mannose, and deoxyglucose. Examples of the disaccharide include lactose and maltose. These saccharides are a concept including enantiomers. For example, Sugar may be D,L-glucose, D-galactose, D-mannose, D-lactose, D-maltose, or deoxyglucose. From the viewpoint of improving water solubility, Sugar may be D-galactose, L-glucose, D-mannose, D-lactose, or D-maltose. From the viewpoint of improving the antitumor activity, Sugar may be D-mannose, D-lactose, or D-maltose. From the viewpoint of synthesis yield, Sugar may be D-lactose. Here, the position of Sugar bonded to an adjacent triazole group is not particularly limited, but may be a carbon atom at the 1-position from the viewpoint of ease of synthesis.

The salt of the compound of the present disclosure is not particularly limited, and examples thereof include a sodium salt, a potassium salt, a calcium salt, and a magnesium salt of the compound of the present disclosure.

The compound or the salt thereof according to the present disclosure has improved water solubility and antitumor activity as compared with the curcumin derivative of Patent Document 1 due to a structure in which a saccharide is added to the DPA site via a linker. The compound or the salt thereof according to the present disclosure has an inhibitory effect on NF-kB, pSTAT3, β-catenin, and/or fatty acid synthetase, thereby exerting the antitumor activity. In addition, the compound or the salt thereof according to the present disclosure further has an angiogenesis inhibitory effect and/or a regulatory T cell suppressive action, and thereby exerts the antitumor activity. The compound or the salt thereof according to the present disclosure has an apoptosis induction potency. The compound or the salt thereof according to the present disclosure can be injected intravenously and exerts the antitumor activity in a mouse model. In addition, safety of the compound or the salt thereof according to the present disclosure has been confirmed in a mouse model.

As described above, the compound or the salt thereof according to the present disclosure has improved water solubility and antitumor activity as compared with the curcumin derivative of Patent Document 1, and safety is also confirmed. Accordingly, the compound or the salt thereof according to the present disclosure can be widely used as an antitumor activator containing the compound or the salt thereof as an active ingredient. The antitumor activator containing the compound or the salt thereof according to the present disclosure as an active ingredient may be an antitumor activator for gastric cancer, an antitumor activator for colorectal cancer, an antitumor activator for pancreatic cancer, an antitumor activator for malignant mesothelioma, or an antitumor activator for cutaneous T-cell lymphoma. In addition, the antitumor activator may be an antitumor activator for gastric cancer, colorectal cancer, pancreatic cancer, malignant mesothelioma, and cutaneous T-cell lymphoma, or an antitumor activator for pancreatic cancer, malignant mesothelioma, and cutaneous T-cell lymphoma. Among them, the antitumor activator may be an antitumor activator for pancreatic cancer. In addition, the compound or the salt thereof according to the present disclosure can be used for various applications as an active ingredient such as an anti-inflammatory agent, an immunotherapeutic agent, or a heart failure protective agent.

Note that for a content of the active ingredient, an optimum amount should be determined in consideration of conditions (general condition, disease state, presence or absence of complication), age, body weight, and the like of a patient. The form of a medical agent is not particularly limited, and a known form such as an oral preparation, an injection, or an inhalation can be used.

Next, a method for producing the compound or the salt thereof according to the present disclosure will be described. The method for producing the compound or the salt thereof according to the present disclosure is not particularly limited, and examples thereof include the following production method (production method of the present disclosure). In the production method of the present disclosure, the following compounds (1) to (3) are used. The compound (1) and the compound (3) are known and can be purchased from reagent companies. The compound (2) can be obtained by a method described in Patent Document 1.

Formula 3

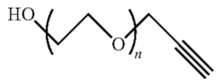

(1)

Formula 4

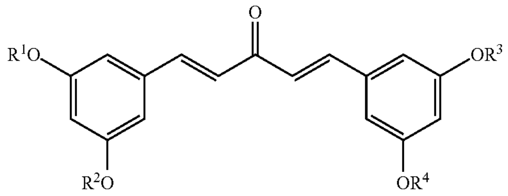

(2)

The method for producing the compound or the salt thereof according to the present disclosure includes a step S1 of acetylthioating a hydroxy group of the compound (1), a step S2 of reacting the acetylthioated compound (1) with the compound (2) to obtain an intermediate A, and a step S3 of reacting the intermediate A with a compound 3 to obtain the compound of the present disclosure. The reaction scheme of each step is indicated below.

Formula 5

Sugar—$N_3$

Formula 6

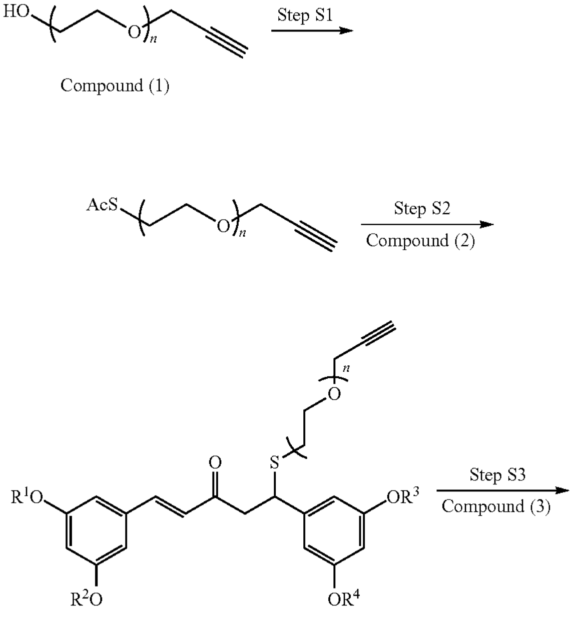

Compound (1)

Intermediate A

-continued

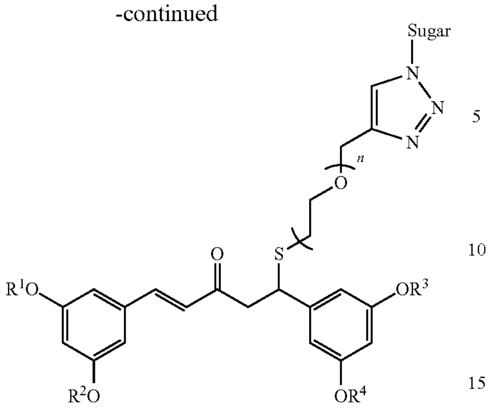

The step S1 is not particularly limited as long as the hydroxyl group of the compound (1) can be acetylthioated. For example, the acetylthioated compound (1) can be obtained by tosylating the hydroxyl group of the compound (1) under a basic condition and then acetylthioating the tosylated compound (1).

The tosylation is carried out by reacting the compound (1) with a halide of p-toluenesulfonic acid under a basic condition. A solvent used for the tosylation is not particularly limited as long as the tosylation can proceed, and examples thereof include ether. A method for obtaining the basic condition is not particularly limited, and for example, the basic condition can be obtained by dissolving potassium hydroxide in a solvent. A specific method of the tosylation will be described in Examples below.

The acetylthiolation is carried out by reacting the tosylated compound (1) with thioacetic acid or a salt thereof. A solvent used for the acetylthiolation is not particularly limited, and examples thereof include DMF. A specific method of the acetylthiolation will be described in Examples below.

The step S2 is not particularly limited as long as the acetylthioated compound (1) and the compound (2) can be reacted with each other to obtain the intermediate A. For example, the intermediate A can be obtained by thiolating the acetylthiolated compound (1) and then reacting the thiolated compound (1) with the compound (2).

The thiolation proceeds by adding an alkoxide to an alcohol solution of the acetylthiolated compound (1). A specific method of the thiolation will be described in Examples below.

The reaction between the thiolated compound (1) and the compound (2) proceeds in the presence of a basic compound. A base compound is not particularly limited, and examples thereof include triethylamine. The solvent is not particularly limited and examples thereof include DMF. A specific method of the reaction between the thiolated compound (1) and the compound (2) will be described in Examples below.

Step S3 is not particularly limited as long as the compound of the present disclosure can be obtained by reacting the intermediate A with the compound (3). For example, the compound can be obtained by bonding a triple bond site of the intermediate A and an azide site of the compound (3) by cyclization reaction to form a triazole skeleton.

Cyclization reaction proceeds in the presence of a copper catalyst. The copper catalyst is not particularly limited, and examples thereof include copper 2-thiophenecarboxylate. The solvent is not particularly limited, and examples thereof include a water-containing ether solvent. A specific method of the cyclization reaction will be described in Examples below.

The production method according to the present disclosure may include a step of converting the compounds obtained in step S3 into a salt by neutralization reaction. A method for converting the compound of the present disclosure into a salt by neutralization reaction is not particularly limited, and a known method can be employed. For example, a desired salt can be obtained by dissolving the compound of the present disclosure in a basic solution containing a predetermined metal ion.

EXAMPLES

Hereinafter, the present disclosure will be further described on the basis of Examples. However, the present disclosure is not limited thereto. Compounds used in experiments are indicated in FIGS. 1 to 5.

[Synthesis of Compound]

GO-Y193, 197 to 200, and 206 were synthesized by the following synthesis route. GO-Y196 was also synthesized by the same synthesis route.

Formula 7

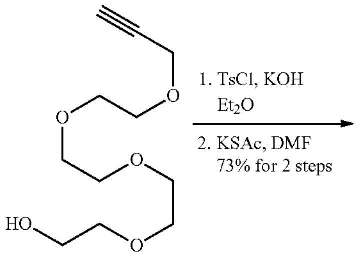

1

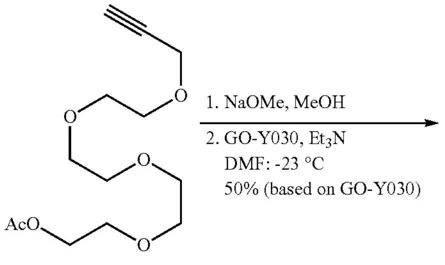

2

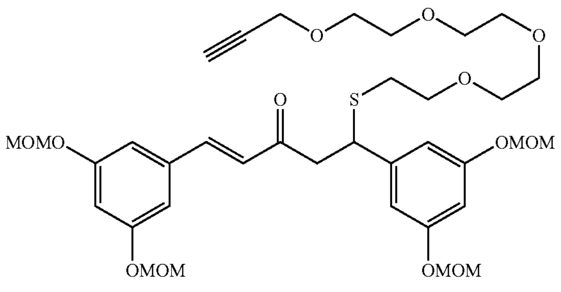

GO-Y030-SPEG$_1$-alkyne 0

-continued

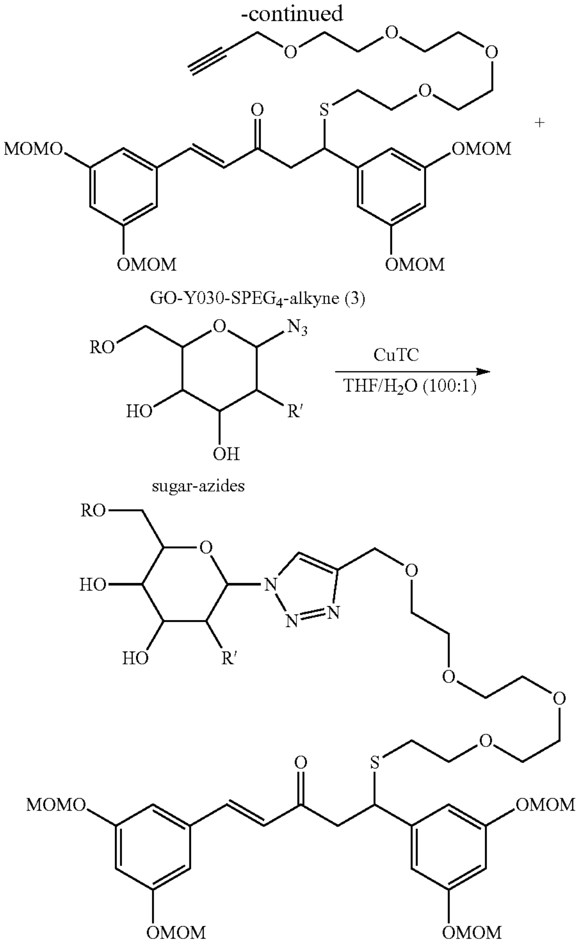

GO-Y030-SPEG$_4$-alkyne (3)

sugar-azides

GO-Y193 (D-glucose): 23% GO-Y197 (L-glucose): 64%
GO-Y196 (D-mannose): 32% GO-Y199(D-lactose): 62%
GO-Y200 (D-maltose): 35% GO-Y206 (deoxyglucose): 61%

<Synthesis of Compound 2>

Potassium hydroxide (2.85 g, 20.0 mmol) was added at 0° C. to 3,6,9,12-tetraoxapentadec-14-yn-1-ol (compound 1, 3.87 g, 16.7 mmol) in diethyl ether (25 mL). After stirring the mixture at 0° C. for 10 minutes, p-toluenesulfonyl chloride (3.82 g, 20.0 mmol) was added thereto and stirring was continued at room temperature for 50 minutes. The reaction was quenched by adding half-saturated aqueous ammonium chloride (50 mL), and then the mixture was extracted with ethyl acetate (160 mL+80 mL). The organic layers were collectively washed with saturated brine (80 mL), and then dried over anhydrous sodium sulfate. The solution subjected to cotton plug filtration was concentrated under reduced pressure to obtain a crude product (6.67 g) which was usable in the subsequent step.

S-potassium acetate (2.30 g, 20.0 mmol) was added at 0° C. to the crude product (crude tosylate) in N,N-dimethylformamide (20 mL). After stirring the mixture at room temperature for 2.5 hours, saturated aqueous sodium bicarbonate solution (50 mL) was added thereto to quench the reaction. The resulting mixture was subjected to cotton plug filtration and the filtrate was extracted with diethyl ether (4×100 mL). The organic layers were collectively washed with saturated brine (100 mL), and dried over anhydrous sodium sulfate. The crude product (10.7 g) obtained by concentrating the solution subjected to cotton plug filtration under reduced pressure was purified by flash column chromatography (silica gel 50 g, n-hexane/ethyl acetate 3:1→ethyl acetate) to obtain S-3,6,9,12-tetraoxapentadec-14-yn-1-yl thioacetate (compound 2, 3.54 g, two-step yield 73%) as an orange oily compound.

(Compound Data of Compound 2)

$R_f$ 0.63 (AcOEt); IR (neat) 3259, 2869, 2113, 1692, 1456, 1353, 1292, 1249, 1105, 1034, 954 $cm^{-1}$; $^1H$ NMR (400 MHz, $CDCl_3$) δ 2.34 (s, 3H), 2.43 (t, J=2.3 Hz, 1H), 3.09 (t, J=6.5 Hz, 2H), 3.60 (t, J=6.5 Hz, 2H), 3.63-3.72 (m, 12H), 4.21 (d, J=2.3 Hz, 2H); $^{13}C$ NMR (100 MHz, $CDCl_3$) δ 28.8, 30.5, 58.4, 69.1, 69.7, 70.3, 70.4, 70.5, 70.6, 74.4, 74.5, 79.6, 195.5; HRMS (FAB) m/z $[M+H]^+$ calcd for $C_{13}H_{23}O_5S$ 291.1261; found 291.1238.

<Synthesis of Compound 3>

Sodium methoxide (347 mg, 6.42 mmol) was added at 0° C. to the compound 2 (620 mg, 2.13 mmol) in methanol (10 mL). After stirring the mixture at room temperature for 1.5 hours, a cation exchange resin (Dowex 50 W×8) was added thereto to neutralize the reaction solution. After celite filtration, the filtrate was concentrated under reduced pressure to obtain a crude product (734 mg) which was usable in the subsequent step.

GO-Y030 (1.02 g, 2.14 mmol) and triethyl amine (0.35 mL, 2.52 mmol) were dissolved in N,N-dimethylformamide (6.0 mL). The crude thiol in N,N-dimethylformamide (12 mL+2 mL for washing) was added slowly at 23° C. thereto. After stirring at the same temperature (23° C.) for 2 hours, water (50 mL) was added thereto. The resulting mixture was extracted with diethyl ether (3×100 mL). The organic layers were collectively washed with saturated brine (150 mL), and then dried over anhydrous sodium sulfate. The crude product (1.89 g) obtained by concentrating the solution subjected to cotton plug filtration under reduced pressure was purified by flash column chromatography (silica gel 50 g, n-hexane/ethyl acetate 1:1) to obtain GO-Y030-SPEG$_4$-alkyne (compound 3, 776 mg, yield 50%) as a light yellow oily compound.

Here, GO-YO30 used in the above reaction was (1E,4E)-1,5-bis-[3,5-bis(methoxymethoxy)phenyl]pentadiene-3-one. A method for synthesizing GO-YO30 is described in Patent Document 1.

(Compound Data of Compound 3)

$R_f$ 0.15 (n-Hexane/AcOEt 1:1); IR (neat) 3279, 2901, 2827, 2114, 1688, 1663, 1592, 1454, 1401, 1332, 1281, 1248, 1215, 1146, 1185, 1033, 965 $cm^{-1}$; $^1H$ NMR (400 MHz, acetone-d6) δ 2.56 (t, J=6.5 Hz, 2H), 2.92 (t, J=2.5 Hz, 1H), 3.22 (dd, J=7.3, 16.4 Hz, 1H), 3.30 (dd, J=7.3, 16.4 Hz, 1H), 3.41 (s, 6H), 3.43 (s, 6H), 3.50-3.61 (m, 14H), 4.54 (d, J=2.5 Hz, 2H), 4.53 (t, J=7.3 Hz, 1H), 5.16 (s, 4H), 5.22 (s, 4H), 6.59 (t, J=2.2 Hz, 1H), 6.76 (t, J=2.3 Hz, 1H), 6.78 (d, J=2.3 Hz, 2H), 6.82 (d, J=15.9 Hz, 1H), 7.00 (d, J=2.3 Hz, 2H), 7.57 (d, J=15.9 Hz, 1H); $^{13}C$ NMR (150 MHz, acetone-d6) δ 31.3, 45.6, 47.5, 56.1, 56.2, 58.5, 69.8, 70.9, 71.0, 71.2, 71.6, 75.7, 81.0, 95.1, 95.2, 104.1, 107.7, 110.20, 110.23, 127.8, 137.7, 143.1, 145.7, 159.3, 159.6, 197.0; HRMS (FAB) m/z $[M+H]^+$ calcd for $C_{36}H_{51}O_{13}S$ 723.3045; found 723.3062.

<Synthesis of GO-Y193>

The compound 3 (214 mg, 296 μmol) and azide (358 mg, 1.75 mmol) were dissolved in water-containing tetrahydrofuran (8.1 mL, tetrahydrofuran:water=100:1). Copper 2-thiophenecarboxylate (4.1 mg, 21.5 μmol) was added thereto, followed by stirring at room temperature for 2 hours. The residue obtained by concentrating the reaction solution under reduced pressure was purified by flash column chromatography (silica gel 2.4 g, chloroform/methanol 19:1→9:1) to obtain GO-Y193 (62.0 mg, yield 23%) as a colorless amorphous substance.

(Compound Data of GO-Y193)

$R_f$ 0.67 ($CHCl_3$/MeOH 4:1); IR (neat) 3398, 1688, 1660, 1593, 1455, 1401, 1281, 1215, 1146, 1085, 1033, 924 $cm^{-1}$; $^1H$ NMR (600 MHz, $CD_3OD$) δ 2.55 (t, J=6.5 Hz, 2H), 3.18 (dd, J=7.0, 16.1 Hz, 1H), 3.24 (dd, J=7.9, 16.1 Hz, 1H), 3.41 (s, 6H), 3.44 (s, 6H), 3.50-3.64 (m, 17H), 3.72 (dd, J=5.5, 12.2 Hz, 1H), 3.88 (dd, J=2.0, 12.2 Hz, 1H), 3.90 (t, J=9.0 Hz, 1H), 4.47 (dd, J=7.0, 7.9 Hz, 1H), 4.62 (s, 2H), 5.12 (d, J=2.2 Hz, 2H), 5.13 (d, J=2.2 Hz, 2H), 5.18 (s, 4H), 5.60 (d, J=9.1 Hz, 1H), 6.59 (d, J=2.2 Hz, 1H), 6.75 (d, J=16.1 Hz, 1H), 6.76 (t, J=2.2 Hz, 1H), 6.76 (d, J=2.2 Hz, 2H), 6.92 (d, J=2.2 Hz, 2H), 7.48 (d, J=16.1 Hz, 1H), 8.15 (s, 1H); $^{13}C$ NMR (150 MHz, $CD_3OD$) δ 31.6 ($CH_2$), 46.4 (CH), 48.0 ($CH_2$), 56.3 ($CH_3$), 56.4 ($CH_3$), 62.4 ($CH_2$), 64.9 ($CH_2$), 70.8 ($CH_2$), 70.9 (CH), 71.3 ($CH_2$), 71.51 ($CH_2$), 71.53 ($CH_2$), 71.55 ($CH_2$), 72.0 ($CH_2$), 74.0 (CH), 78.5 (CH), 81.1 (CH), 89.5 (CH), 95.5 ($CH_2$), 95.6 ($CH_2$), 104.7 (CH), 108.2 (CH), 110.6 (CH), 110.7 (CH), 124.3 (CH), 127.8 (CH), 137.9 (C), 144.6 (CH), 145.8 (C), 146.1 (C), 159.7 (C), 160.0 (C), 199.5 (C); HRMS (FAB) m/z $[M+H]^+$ calcd for $C_{42}H_{62}N_3O_{18}S$ 928.37442; found 928.3762.

<Synthesis of GO-Y197>

The compound 3 (372 mg, 515 μmol), azide (164 mg, 799 μmol), water-containing tetrahydrofuran (10 mL, tetrahydrofuran:water=100:1), and copper 2-thiophenecarboxylate (5.2 mg, 27.3 μmol) were used. The residue obtained by concentrating the reaction solution under reduced pressure was purified by flash column chromatography (silica gel 10 g, ethyl acetate→ethyl acetate/methanol 9:1) to obtain GO-Y197 (307 mg, yield 64%) as a colorless amorphous substance.

(Compound Data of GO-Y197)

$R_f$ 0.10 (AcOEt/MeOH 9:1); IR (neat) 3399, 2903, 1662, 1593, 1455, 1401, 1281, 1215, 1146, 1085, 1033, 924 $cm^{-1}$; $^1H$ NMR (600 MHz, $CD_3OD$) δ 2.53 (t, J=6.2 Hz, 2H), 3.18 (dd, J=6.9, 16.0 Hz, 1H), 3.23 (dd, J=7.9, 16.0 Hz, 1H), 3.39 (s, 6H), 3.42 (s, 6H), 3.50-3.62 (m, 17H), 3.71 (dd, J=5.1, 12.2 Hz, 1H), 3.87 (d, J=12.2 Hz, 1H), 3.91 (t, J=9.1 Hz, 1H), 4.46 (dd, J=6.9, 7.9 Hz, 1H), 4.61 (s, 2H), 5.11 (d, J=6.8 Hz, 2H), 5.15 (d, J=6.8 Hz, 2H), 5.16 (s, 4H), 5.61 (d, J=9.1 Hz, 1H), 6.58 (t, J=2.0 Hz, 1H), 6.73 (d, J=16.1 Hz, 1H), 6.75 (t, J=2.1 Hz, 1H), 6.75 (d, J=2.0 Hz, 2H), 6.91 (d, J=2.0 Hz, 2H), 7.46 (d, J=16.1 Hz, 1H), 8.19 (s, 1H); $^{13}C$ NMR (150 MHz, $CD_3OD$) δ 31.6 ($CH_2$), 46.3 (CH), 48.0 ($CH_2$), 56.38 ($CH_3$), 56.43 ($CH_3$), 62.4 ($CH_2$), 65.0 ($CH_2$), 70.78 ($CH_2$), 70.82 (CH), 71.2 ($CH_2$), 71.43 ($CH_2$), 71.46 ($CH_2$), 71.49 ($CH_2$), 71.9 ($CH_2$), 74.0 (CH), 78.4 (CH), 81.1 (CH), 89.6 (CH), 95.5 ($CH_2$), 95.6 ($CH_2$), 104.7 (CH), 108.2 (CH), 110.6 (CH), 110.7 (CH), 124.8 (CH), 127.8 (CH), 137.9 (C), 144.5 (CH), 145.8 (C), 159.7 (C), 159.9 (C), 199.4 (C); HRMS (FAB) m/z $[M+H]^+$ calcd for $C_{42}H_{62}N_3O_{18}S$ 928.3744; found 928.3742.

<Synthesis of GO-Y198>

The compound 3 (247 mg, 342 μmol), azide (127 mg, 340 μmol), water-containing tetrahydrofuran (7.0 mL, tetrahydrofuran:water=100:1), and copper 2-thiophenecarboxylate (5.2 mg, 27.3 μmol) were used. The residue obtained by concentrating the reaction solution under reduced pressure was purified by flash column chromatography (silica gel 2.3 g, chloroform/methanol 19:1→9:1) to obtain GO-Y198 (102 mg, yield 32%) as a colorless amorphous substance.

(Compound Data of GO-Y198)

$R_f$ 0.13 (AcOEt/MeOH 9:1); IR (neat) 3399, 2903, 1685, 1654, 1593, 1456, 1400, 1332, 1281, 1215, 1146, 1084, 1033, 924 $cm^{-1}$; $^1H$ NMR (600 MHz, $CD_3OD$) δ 2.53 (t, J=6.5 Hz, 2H), 3.16 (dd, J=7.0, 15.8 Hz, 1H), 3.20 (dd, J=7.9, 15.8 Hz, 1H), 3.39 (s, 6H), 3.43 (s, 6H), 3.49-3.52 (m, 4H), 3.55-3.63 (m, 11H), 3.72-3.82 (m, 3H), 4.07 (dd, J=3.3, 8.7 Hz, 1H), 4.45 (dd, J=6.9, 7.9 Hz, 1H), 4.68 (t, J=3.3 Hz, 1H), 4.80 (s, 2H), 5.11 (d, J=6.8 Hz, 2H), 5.14 (d, J=6.8 Hz, 2H), 5.16 (s, 4H), 6.02 (d, J=2.6 Hz, 1H), 6.57 (d, J=2.1 Hz, 1H), 6.72 (d, J=16.1 Hz, 1H), 6.74 (t, J=2.1 Hz, 1H), 6.74 (d, J=2.0 Hz, 2H), 6.90 (d, J=2.0 Hz, 2H), 7.46 (d, J=16.1 Hz, 1H), 8.12 (s, 1H); $^{13}C$ NMR (150 MHz, $CD_3OD$) δ 31.6 ($CH_2$), 46.3 (CH), 48.0 ($CH_2$), 56.37 ($CH_3$), 56.42 ($CH_3$), 62.5 ($CH_2$), 64.9 ($CH_2$), 68.5 (CH), 70.1 (CH), 70.8 ($CH_2$), 71.2 ($CH_2$), 71.45 ($CH_2$), 71.48 ($CH_2$), 71.51 ($CH_2$), 71.9 ($CH_2$), 72.5 (CH), 78.5 (CH), 88.3 (CH), 95.5 ($CH_2$), 95.6 ($CH_2$), 104.7 (CH), 108.2 (CH), 110.6 (CH), 110.7 (CH), 125.0 (CH), 127.8 (CH), 137.9 (C), 144.5 (CH), 145.8 (C), 146.3 (C), 159.7 (C), 159.9 (C), 199.3 (C); HRMS (FAB) m/z $[M+H]^+$ calcd for $C_{42}H_{62}N_3O_{18}S$ 928.3744; found 928.3752.

<Synthesis of GO-Y199>

The compound 3 (214 mg, 296 μmol), azide (109 mg, 296 μmol), water-containing tetrahydrofuran (6.0 mL, tetrahydrofuran:water=100:1), and copper 2-thiophenecarboxylate (6.2 mg, 32.5 μmol) were used. The residue obtained by concentrating the reaction solution under reduced pressure was purified by flash column chromatography (twice: silica gel 3 g, chloroform/methanol 9:1→4:1, silica gel 2.3 g, chloroform/methanol 9:1→17:3) to obtain GO-Y199 (199 mg, yield 62%) as a colorless amorphous substance.

(Compound Data of GO-Y199)

$R_f$ 0.20 ($CHCl_3$/MeOH 4:1); IR (neat) 3389, 1660, 1593, 1455, 1440, 1401, 1333, 1281, 1241, 1215, 1146, 1084, 1034, 924 $cm^{-1}$; $^1H$ NMR (600 MHz, $CD_3OD$) δ 2.55 (t, J=6.6 Hz, 2H), 3.18 (dd, J=7.1, 15.9 Hz, 1H), 3.23 (dd, J=7.9, 15.9 Hz, 1H), 3.41 (s, 6H), 3.45 (s, 6H), 3.47-3.64 (m, 17H), 3.74-3.83 (m, 6H), 3.89 (m, 2H), 3.97 (t, J=9.1 Hz, 1H), 4.41 (d, J=7.8 Hz, 1H), 4.47 (dd (dd, J=6.6, 7.9 Hz, 1H), 4.62 (s, 2H), 5.12 (d, J=6.9 Hz, 2H), 5.14 (d, J=6.9 Hz, 2H), 5.18 (s, 4H), 5.63 (d, J=9.1 Hz, 1H), 6.58 (d, J=2.2 Hz, 1H), 6.74 (d, J=16.2 Hz, 1H), 6.76 (t, J=2.1 Hz, 1H), 6.76 (d, J=2.2 Hz, 2H), 6.92 (d, J=2.1 Hz, 2H), 7.48 (d, J=16.2 Hz, 1H), 8.16 (s, 1H); $^{13}C$ NMR (150 MHz, $CD_3OD$) δ 31.6 ($CH_2$), 46.4 (CH), 48.1 ($CH_2$), 56.3 ($CH_3$), 56.4 ($CH_3$), 61.6 ($CH_2$), 62.5 ($CH_2$), 65.0 ($CH_2$), 70.3 (CH), 70.8 ($CH_2$), 71.3 ($CH_2$), 71.51 ($CH_2$), 71.56 ($CH_2$), 71.57 ($CH_2$), 71.59 ($CH_2$), 72.0 ($CH_2$), 72.5 (CH), 73.7 (CH), 74.9 (CH), 76.9 (CH), 77.1 (CH), 79.6 (CH), 79.8 (CH), 89.3 (CH), 95.56 ($CH_2$), 95.62 ($CH_2$), 104.8 (CH), 105.1 (CH), 108.2 (CH), 110.65 (CH), 110.72 (CH), 124.3 (CH), 127.8 (CH), 137.9 (C), 144.6 (CH), 145.8 (C), 146.1 (C), 159.8 (C), 160.0 (C), 199.6 (C); HRMS (FAB) m/z $[M+H]^+$ calcd for $C_{48}H_{72}N_3O_{23}S$ 1090.4272; found 1090.4265.

<Synthesis of GO-Y200>

The compound 3 (226 mg, 313 μmol), azide (160 mg, 436 μmol), water-containing tetrahydrofuran (10 mL, tetrahydrofuran:water=100:1), and copper 2-thiophenecarboxylate (3.3 mg, 17.3 nmol) were used. The residue obtained by concentrating the reaction solution under reduced pressure was purified by flash column chromatography (silica gel 5.5 g, chloroform/methanol 9:1→17:3) to obtain GO-Y200 (133 mg, yield 35%) as a colorless amorphous substance.

(Compound Data of GO-Y200)

$R_f$ 0.08 ($CHCl_3$/MeOH 8:1); IR (neat) 3386, 2904, 1684, 1661, 1594, 1541, 1506, 1456, 1400, 1334, 1281, 1216, 1146, 1084, 1033, 968 $cm^{-1}$; $^1H$ NMR (600 MHz, $CD_3OD$) δ 2.56 (t, J=6.5 Hz, 2H), 3.18 (dd, J=6.9, 16.0 Hz, 1H), 3.24 (dd, J=7.9, 16.0 Hz, 1H), 3.42 (s, 6H), 3.46 (s, 6H), 3.48 (m, 1H), 3.53-3.56 (m, 4H), 3.59-3.70 (m, 12H), 3.76 (t, J=9.2

Hz, 1H), 3.82-3.90 (m, 4H), 3.96 (t, J=9.2 Hz, 1H), 4.48 (dd J=6.9, 7.9 Hz, 1H), 4.63 (s, 2H), 5.13 (d, J=6.8 Hz, 2H), 5.15 (d, J=6.8 Hz, 2H), 5.19 (s, 4H), 5.24 (d, J=3.9 Hz, 1H), 5.63 (d, J=9.2 Hz, 1H), 6.59 (t, J=2.2 Hz, 1H), 6.75 (d, J=16.3 Hz, 1H), 6.77 (t, J=2.2 Hz, 1H), 6.77 (d, J=2.2 Hz, 2H), 6.94 (d, J=2.2 Hz, 2H), 7.49 (d, J=16.3 Hz, 1H), 8.17 (s, 1H); $^{13}C$ NMR (150 MHz, $CD_3OD$) δ 31.6 ($CH_2$), 46.4 (CH), 48.1 ($CH_2$), 56.3 ($CH_3$), 56.4 ($CH_3$), 61.9 ($CH_2$), 62.8 ($CH_2$), 65.0 ($CH_2$), 70.8 (CH—), 71.3 ($CH_2$), 71.53 (CH), 71.57 ($CH_2$), 71.58 ($CH_2$), 71.60 ($CH_2$), 72.1 ($CH_2$), 73.6 (CH), 74.2 (CH), 74.9 (CH), 75.1 (CH), 78.2 (CH), 79.7 (CH), 80.4 (CH), 89.4 (CH), 95.57 ($CH_2$), 95.63 ($CH_2$), 103.0 (CH), 104.8 (CH), 108.2 (CH), 110.66 (CH), 110.72 (CH), 124.3 (CH), 127.8 (CH), 138.0 (C), 144.6 (CH), 145.8 (C), 146.1 (C), 159.8 (C), 160.0 (C), 199.6 (C); HRMS (FAB) m/z $[M+H]^+$ calcd for $C_{48}H_{72}N_3O_{23}S$ 1090.4272; found 1090.4303.

72.3 (CH), 72.4 (CH), 81.0 (CH), 85.6 (CH), 95.5 ($CH_2$), 95.6 ($CH_2$), 104.7 (CH), 108.2 (CH), 110.6 (CH), 110.7 (CH), 123.8 (CH), 127.8 (CH), 137.9 (C), 144.5 (CH), 145.8 (C), 146.1 (C), 159.7 (C), 159.9 (C), 199.3 (C); HRMS (FAB) m/z $[M+H]^+$ calcd for $C_{42}H_{62}N_3O_{17}S$ 912.3794; found 912.3803.

[Turbidity Measurement]

The turbidity of various compounds was measured. The method is as follows. A compound was once dissolved in DMSO (dimethyl sulfoxide) and then dissolved in distilled water or DMEM medium (Dulbecco's modified Eagle's medium) containing 10% fetal bovine serum to have a final concentration of 50 μM. Curcumin was cloudy while GO-Y199 was clear. The solubility was measured with a turbidimeter (WZB-170 Portable Turbidimeter available from REX). The turbidity of the compound was corrected for concentration. The results are indicated in Table 1.

TABLE 1

| | stock (in DMSO) (mM) | Dilution (in 30 mL DDW) | Final conc. (μm) | Turbidity (NTU) | Ave Turbidity (NTU) | Turbidity/ μm | Relative Value |
|---|---|---|---|---|---|---|---|
| GO-Y190 | 5 | 50 μL | 8.3 | 0.40, 0.53, 0.66 | 0.53 ± 0.11 | 0.064 | 0.22 |
| GO-Y192 | 5 | 50 μL | 8.3 | 0.65, 0.56, 0.65 | 0.62 ± 0.04 | 0.075 | 0.26 |
| GO-Y193 | 100 | 50 μL | 170 | 7.18, 6.15, 5.83 | 6.39 ± 0.58 | 0.038 | 0.13 |
| GO-Y198 | 5 | 50 μL | 8.3 | 0, 0, 0 | 0 | 0 | 0 |
| GO-Y197 | 5 | 50 μL | 8.3 | 0, 0, 0 | 0 | 0 | 0 |
| GO-Y198 | 5 | 50 μL | 8.3 | 0, 0, 0 | 0 | 0 | 0 |
| GO-Y199 | 100 | 50 μL | 170 | 0.03, 0.06, 0.14 | 0.07 ± 0.05 | 0.00041 | 0.0014 |
| GO-Y200 | 5 | 50 μL | 8.3 | 0, 0, 0 | 0 | 0 | 0 |
| GO-Y136 | 1 | 50 μL | 1.7 | 0.05, 0.04, 0.03 | 0.04 ± 0.0082 | 0.024 | 0.083 |
| GO-Y030 | 100 | 50 μL | 170 | over limit | x | x | x |
| GO-Y030 | | 1/10 | 17 | 45.3, 45.6, 45.8 | 45.6 ± 0.21 | 2.68 | 9.2 |
| GO-Y022 | 50 | 5 μL | 8.3 | 0.13, 0.13, 0.11 | 0.12 ± 0.0094 | 0.014 | 0.048 |
| curcumin | 100 | 50 μL | 170 | 49.4, 49.7, 49.8 | 49.6 ± 0.17 | 0.29 | 1 |

<Synthesis of GO-Y206>

The compound 3 (148 mg, 205 μmol), azide (α:β=1:0.7, 116 mg, 613 μmol), water-containing tetrahydrofuran (4.0 mL, tetrahydrofuran:water=100:1), and copper 2-thiophenecarboxylate (8.8 mg, 46.2 μmol) were used. The residue obtained by concentrating the reaction solution under reduced pressure was purified by flash column chromatography (silica gel 5.0 g, chloroform/methanol 1:0→100:3→10:1) to obtain GO-Y206 (113 mg, yield 61%) as a colorless oily substance. Note that FIG. 5 indicates only a compound in which β-deoxyglucose is bonded, but GO-Y206 also includes a compound in which α-deoxyglucose is bonded.

(Compound Data of GO-Y206)

$R_f$ 0.13 (AcOEt/MeOH 9:1); IR (neat) 3416, 2902, 1687, 1661, 1593, 1454, 1400, 1332, 1281, 1215, 1146, 1084, 1033, 924 $cm^{-1}$; $^1H$ NMR (600 MHz, $CD_3OD$) δ 2.19 (q, J=11.8 Hz, 1H), 2.43 (ddd, J=2.0, 4.8, 11.8 Hz, 1H), 2.52 (t, J=6.7 Hz, 2H), 3.18 (dd, J=7.0, 16.0 Hz, 1H), 3.23 (dd, J=7.4, 16.0 Hz, 1H), 3.39 (t, J=9.3 Hz, 1H), 3.40 (s, 6H), 3.43 (s, 6H), 3.49-3.63 (m, 15H), 3.72 (dd, J=5.4, 12.0 Hz, 1H), 3.79 (m, 1H), 3.89 (dd, J=2.3, 12.0 Hz, 1H), 4.46 (t, J=7.4 Hz, 1H), 4.60 (s, 2H), 5.11 (d, J=7.0 Hz, 2H), 5.13 (d, J=7.0 Hz, 2H), 5.17 (s, 4H), 5.90 (dd, J=2.0, 11.8 Hz, 1H), 6.58 (t, J=2.2 Hz, 1H), 6.74 (d, J=16.1 Hz, 1H), 6.75 (m, 3H), 6.91 (d, J=2.2 Hz, 2H), 7.48 (d, J=16.1 Hz, 1H), 8.15 (s, 1H); $^{13}C$ NMR (150 MHz, $CD_3OD$) δ 31.6 ($CH_2$), 39.4 ($CH_2$), 46.3 (CH), 48.0 ($CH_2$), 56.8 ($CH_3$), 56.43 ($CH_3$), 62.5 ($CH_2$), 64.9 ($CH_2$), 70.8 ($CH_2$), 71.2 ($CH_2$), 71.45 ($CH_2$), 71.49 ($CH_2$), 71.51 ($CH_2$), 71.53 ($CH_2$), 71.9 ($CH_2$), From Table 1, it was confirmed that the turbidities of GO-Y196 to 200 were 0 or very small, and the water solubility was improved as compared with GO-Y030 and curcumin.

Subsequently, GO-Y206 and curcumin were adjusted to final concentrations of 1.25 μM and 5.00 μM, respectively, and their turbidities were measured. The results are indicated in Table 2.

TABLE 2

| | Final conc. (μm) | Turbidity (NTU) | Turbidity/ μm | Relative Value |
|---|---|---|---|---|
| GO-Y206 | 5.0 | 1.82 | 0.364 | Ave. 0.254 |
| GO-Y206 | 11.25 | 0.18 | 0.144 | (0.052) |
| curcumin | 5.0 | 29.0 | 5.8 | Ave. 4.884 |
| curcumin | 1.25 | 4.96 | 3.968 | (1.00) |

The turbidity of GO-Y206 having a final concentration of 1.25 μM was 0 18 NTU, and the turbidity of GO-Y206 having a final concentration of 5.00 μM was 1 82 NTU. On the other hand, the turbidities of curcumin having final concentrations of 1.25 μM and 5.00 μM were 4.96 NTU and 29.0 NTU, respectively. The values of NTU were divided by the concentrations, respectively, and the resulting values were averaged to give 0.254 NTU/μM for GO-Y206 and 4.884 NTU/μM for curcumin. Thus, the turbidity of GO-Y206 was improved to 5% of curcumin.

[Cell Growth Inhibitory Activity and Turbidity]

Figure 6:
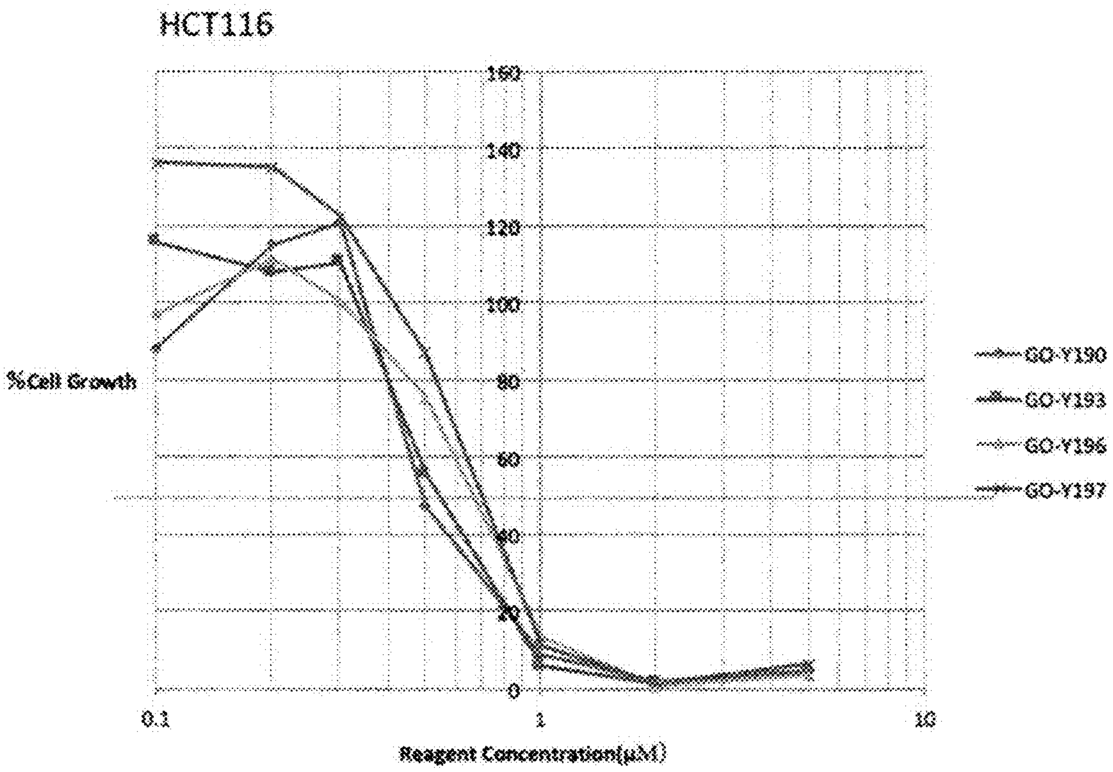
FIG. 6 indicates experimental results of a cell growth inhibitory activity of GO-Y190, GO-Y193, GO-Y196, and GO-Y197 on HCT116.

The cell growth inhibitory activity against a colorectal cancer cell line HCT116 was measured. As an index of cell growth inhibitory activity, a concentration at which cell growth was inhibited by 50% as compared with a control ($IC_{50}$) was used. The method is as follows. HCT116 was added to a 6-well plate by $5\times10^4$, compounds having various concentrations were added after 24 hours, and the number of cells was counted after 72 hours of culture. As the control, DMSO was used in an amount equal to the amount added in accordance with the addition concentration of the highest-concentration compound. The number of cells at each concentration relative to the control was expressed as a percentage. The results are indicated in Table 2. In Table 3, the turbidities of the compounds are also indicated. FIG. 6 indicates the measurement results of the cell growth inhibitory activity of GO-Y190, GO-Y193, GO-Y196, and GO-Y197.

TABLE 3

| | IC50 (μm) | Turbidity (Relative Value) |
|---|---|---|
| GO-Y190 | 0.48 | 0.22 |
| GO-Y191 | 0.4 | x |
| GO-Y192 | 0.6 | 0.26 |
| GO-Y193 | 0.55 | 0.13 |
| GO-Y194 | 0.5 | x |
| GO-Y195 | 1.8 | x |
| GO-Y196 | 0.67 | 0 |
| GO-Y197 | 0.7 | 0 |
| GO-Y198 | 0.44 | 0 |
| GO-Y199 | 0.43 | 0.0014 |
| GO-Y200 | 0.42 | 0 |
| Curcumin | 16 | 1 |
| GO-Y030 | 0.71 | 9.2 |
| GO-Y022 | 2.02 | 0.048 |
| GO-Y136 | 0.89 | 0.083 |
| M1797 | >5.0 | x |

As indicated in Table 3, GO-Y190 to 194 and 196 to 200 had a higher cell growth inhibitory activity than that of GO-Y030 and curcumin. Among them, GO-Y190, 191, and 198 to 200 had a particularly high cell growth inhibitory activity. Furthermore, among them, GO-Y198 to 200 were excellent in water solubility. GO-Y199 can be synthesized with the highest yield among them, and thus, the following experiment was carried out focusing on GO-Y199.

[Cell Growth Inhibitory Activity on Various Cancer Cell Lines]

Figure 7:
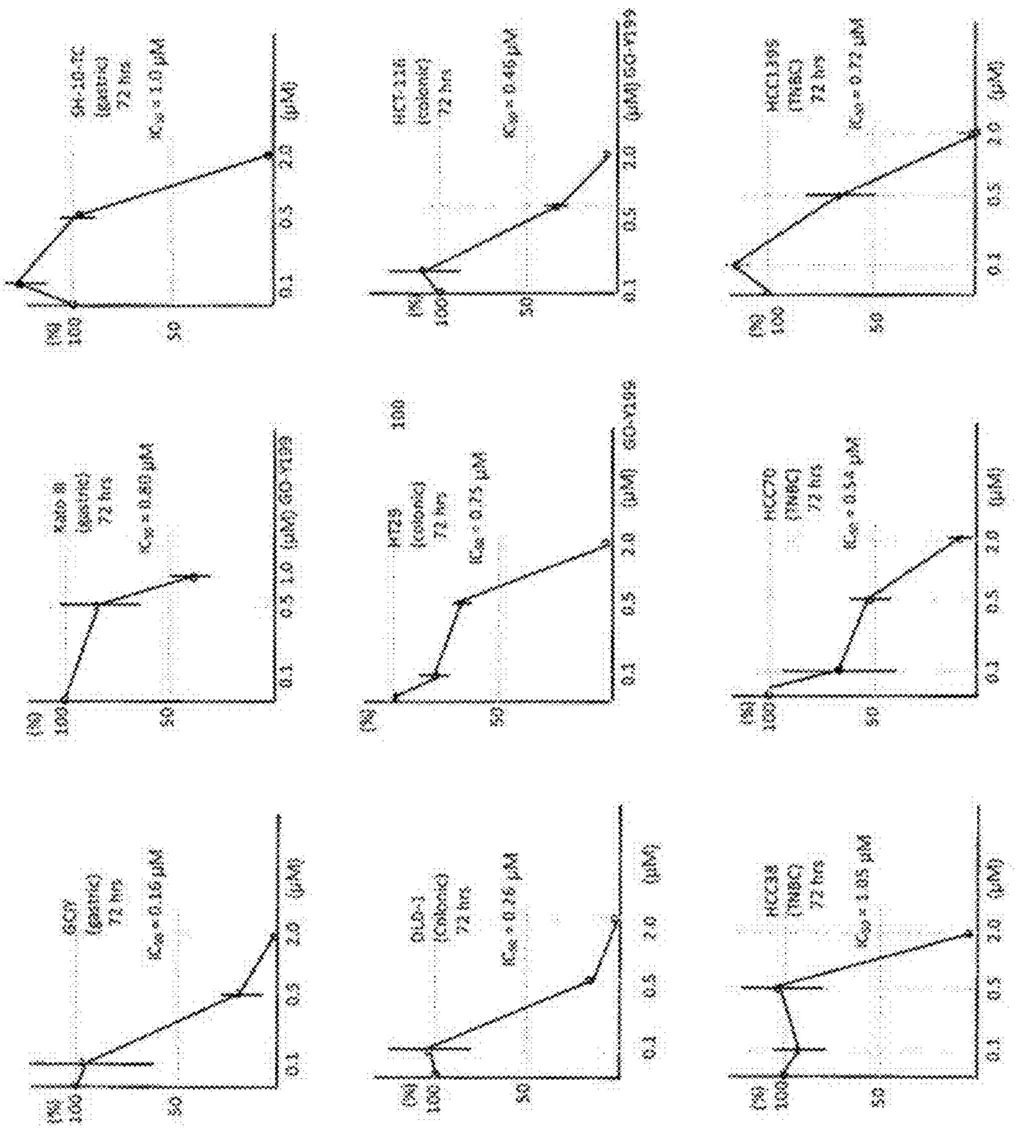
FIG. 7 indicates experimental results of a cell growth inhibitory activity of GO-Y199 against various cancer cell lines.

($IC_{50}$) of the cell growth inhibitory activity of each of curcumin, GO-Y030, GO-Y193, and GO-Y199 against various cancer cell lines (gastric cancer cell lines: GCIY, Kato III, SH-10-TC, colorectal cancer cell lines: DLD-1, HT29, HCT-116, breast cancer cell lines: HCC38, HCC70, HCC1395) was measured. The method is as described above. The results are indicated in Table 4. In Table 5, the $IC_{50}$ was compared between GO-Y199 and curcumin, and between GO-Y199 and GO-Y030. FIG. 7 indicates the results of the cell growth inhibitory activity of GO-Y199 against various cancer cell lines.

TABLE 4

| | HCC1395 | HCC38 | HOC701 | SH-10-TC | KATO III |
|---|---|---|---|---|---|
| GO-Y193 (μM) | 0.6 | 1.3 | 1.15 | 0.92 | 0.92 |
| GO-Y199 (μM) | 0.72 | 1.05 | 0.54 | 1 | 0.8 |
| GO-Y030 (μM) | 2.09 | 1.8 | 2.28 | 1.54 | x |
| curcumin (μM) | x | x | x | 8.07 | x |

TABLE 4-continued

| | GCIY | HCT-116 | DLD-1 | HT29 |
|---|---|---|---|---|
| GO-Y193 (μM) | 0.28 | 0.72 | 0.75 | 0.45 |
| GO-Y199 (μM) | 0.16 | 0.46 | 0.28 | 0.75 |
| GO-Y030 (μM) | 0.21 | 0.71 | 0.73 | x |
| curcumin (μM) | 8.66 | 16.01 | 18.74 | x |

TABLE 5

| | HCC1395 | HCC38 | HCC70 | SH-10-TC | KATO III |
|---|---|---|---|---|---|
| GO-Y199 vs curcumin | x | x | x | 0.124 | x |
| GO-Y199 vs GO-Y030 | 0.34 | 0.58 | 0.24 | 0.65 | x |
| | **GCIY** | **HCT-116** | **DLD-1** | **HT29** | |
| GO-Y199 vs curcumin | 0.03 | 0.029 | 0.014 | x | |
| GO-Y199 vs GO-Y030 | 1.24 | 0.65 | 0.36 | x | |

As indicated in Table 4, GO-Y193 and GO-Y199 had a high cell growth inhibitory activity against any of the cancer cell lines. In addition, as indicated in Table 5, GO-Y199 had an antitumor activity of 33.3 to 71.4 times that of curcumin, and had an antitumor activity of 0.8 to 4.2 times that of GO-Y030. From this result, it can be said that GO-Y199 has a higher antitumor activity than that of curcumin and GO-Y030.

Figure 8:
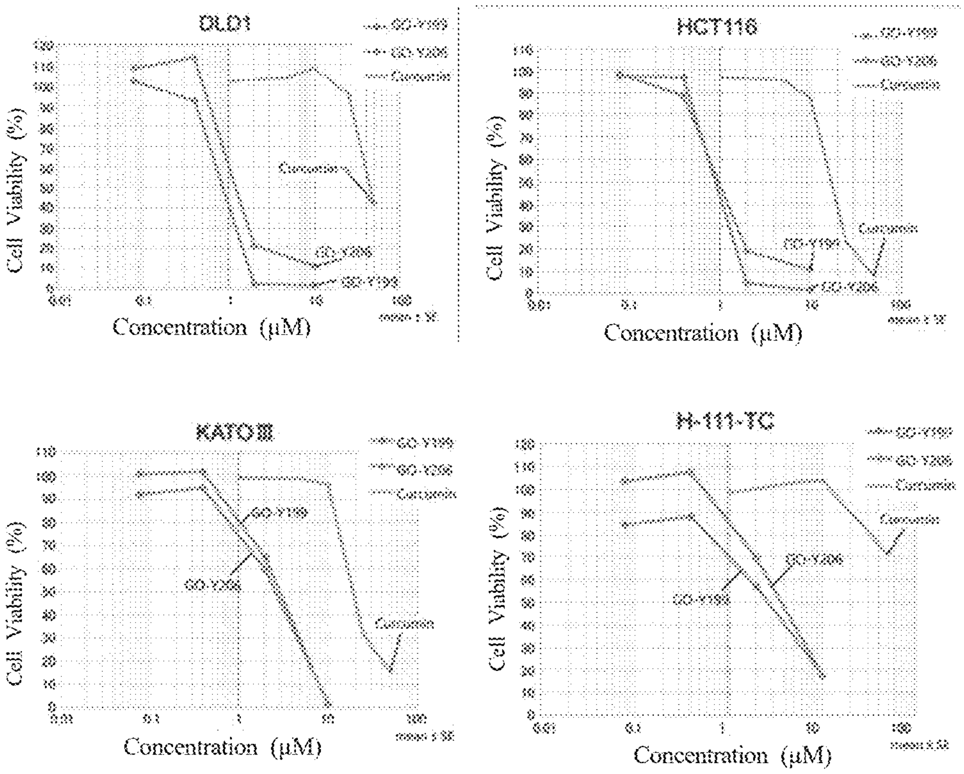
FIG. 8 indicates experimental results of a cell growth inhibitory activity of various compounds against colorectal cancer cell lines DLD-1 and HCT116, and gastric cancer cell lines KATO III and H-111-TC.

The cell growth inhibitory activity ($IC_{50}$) of each of curcumin, GO-Y199, and GO-Y206 against the colorectal cancer cell lines DLD-1 and HCT116 and the gastric cancer cell lines KATO III and H-111-TC was measured. The method is as described above. The results are indicated in Table 6. FIG. 8 indicates the results of cell growth inhibitory activity of these compounds against various cancer cell lines.

TABLE 6

| | $IC_{50}$ (μm) | | | |
|---|---|---|---|---|
| | DLD-1 | HCT116 | KATO III | H-111-TC |
| Curcumin | 44.84 | 7.08 | 11.03 | > 50.0 |
| GO-Y199 | 0.85 | 0.98 | 3.86 | 2.9 |
| GO-Y206 | 1.21 | 0.91 | 3.11 | 4.67 |

As indicated in Table 6, GO-Y199 and GO-Y206 had a high cell growth inhibitory activity against any of the colorectal cancer cell lines as compared with curcumin. In addition, the effect of GO-Y206 was equivalent to that of GO-Y199.

Figure 9:
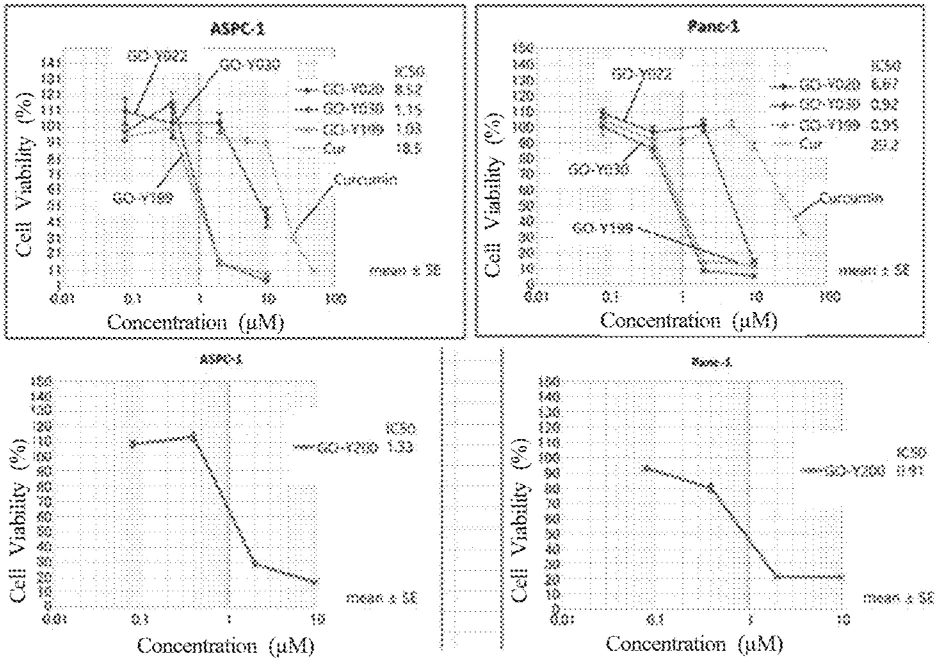
FIG. 9 indicates experimental results of a cell growth inhibitory activity of various compounds against pancreatic cancer cell lines ASPC-1 and Panc-1.

The cell growth inhibitory activity ($IC_{50}$) of each of curcumin, GO-Y022, GO-Y030, GO-Y199, and GO-Y200 against pancreatic cancer cell lines ASPC-1 and Panc-1 was measured. The method is as described above. The results are indicated in Table 7. FIG. 9 indicates the results of the cell growth inhibitory activity of these compounds against various cancer cell lines.

TABLE 7

| | $IC_{50}$ (μm) | |
|---|---|---|
| | ASPC-1 | Panc-1 |
| Curcumin | 18.5 | 29.2 |
| GO-Y022 | 8.52 | 6.67 |
| GO-Y030 | 1.15 | 0.92 |
| GO-Y199 | 1.03 | 0.95 |
| GO-Y200 | 1.33 | 0.91 |

As indicated in Table 7, GO-Y199 and GO-Y200 had a high cell growth inhibitory activity against any of the pancreatic cancer cell lines as compared with curcumin. In addition, GO-Y199 and GO-Y200 had a high effect as compared with GO-Y022.

Figure 10:
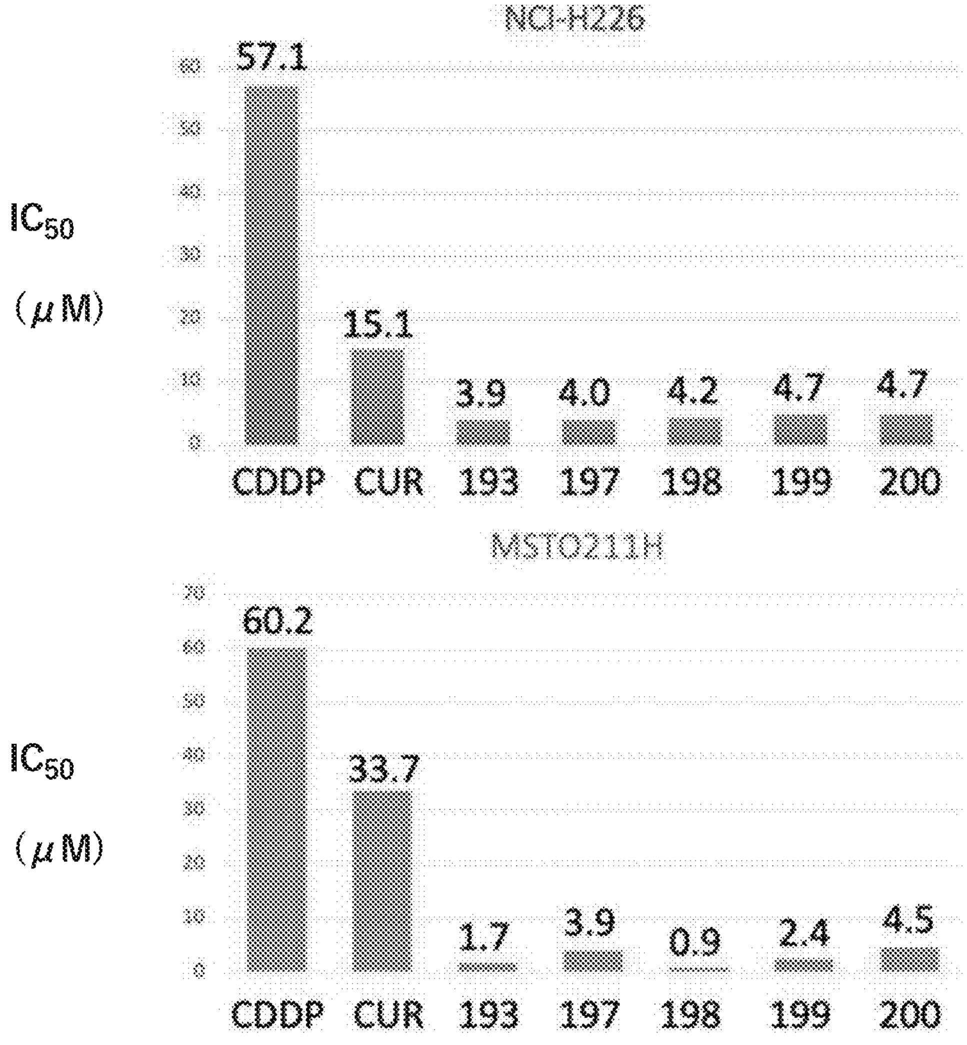
FIG. 10 indicates experimental results of a cell growth inhibitory activity ($IC_{50}$) of various compounds against malignant pleural mesothelioma cell lines NCI-H226 and MSTO211H.

The cell growth inhibitory activity ($IC_{50}$) of each of curcumin, GO-Y193, GO-Y197. GO-Y198, GO-Y199, and GO-Y200 against malignant pleural mesothelioma cell lines NCI-H226 and MSTO211H was measured. The method is as described above. The results are indicated in Table 8 and FIG. 10. For comparison, the $IC_{50}$ of cisplatin (CDDP), a cytocidal anticancer agent, is also indicated.

TABLE 8

| | $IC_{50}$ (μm) | |
|---|---|---|
| | NCI-H226 | MSTO211H |
| Curcumin | 15.1 | 33.7 |
| GO-Y193 | 3.9 | 1.7 |
| GO-Y197 | 4.0 | 3.9 |
| GO-Y198 | 4.2 | 0.9 |
| GO-Y199 | 4.7 | 2.4 |
| GO-Y200 | 4.7 | 4.5 |

From Table 8, GO-Y193, GO-Y197, GO-Y198, GO-Y199, and GO-Y200 had a high cell growth inhibitory activity against any of the malignant pleural mesothelioma cell lines as compared with curcumin.

Figure 11:
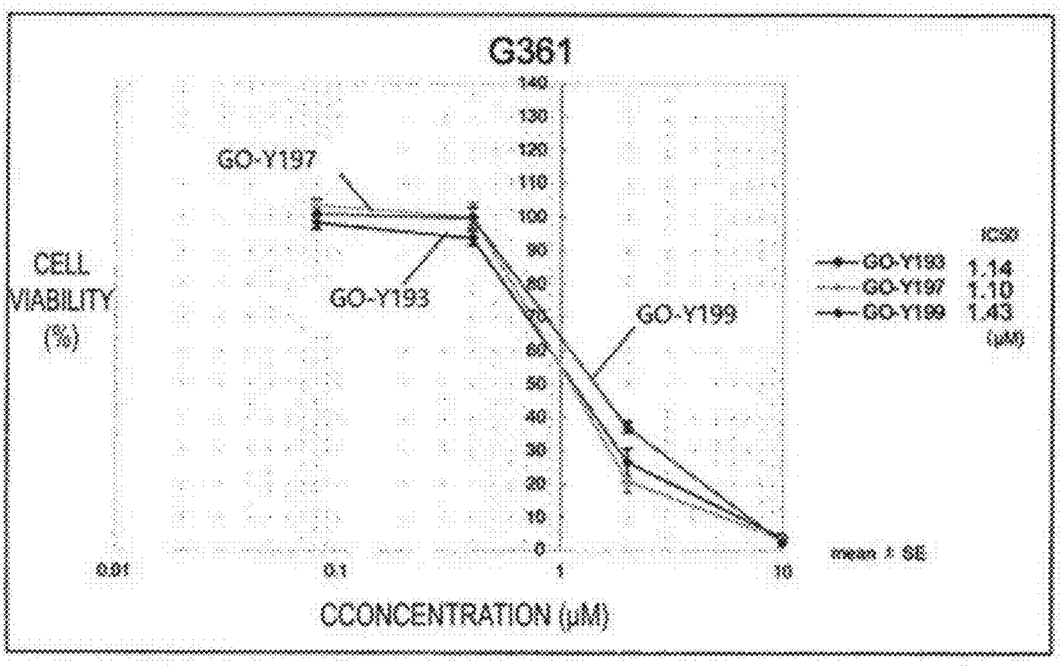
FIG. 11 indicates experimental results of a cell growth inhibitory activity of various compounds against a malignant melanoma cell line G361.

The cell growth inhibitory activity ($IC_{50}$) of each of curcumin, GO-Y022, GO-Y030, GO-Y193, GO-Y197, and GO-Y199 against the malignant melanoma cell line G361 was measured. The method is as described above. The results are indicated in Table 9. FIG. 11 indicates the results of the cell growth inhibitory activity of GO-Y193, GO-Y197, and GO-Y199 as representatives against the melanoma cell line.

TABLE 9

| | $IC_{50}$ (μm) G361 |
|---|---|
| Curcumin | 16.8 |
| GO-Y022 | 3.1 |
| GO-Y030 | 2 |
| GO-Y193 | 1.1 |
| GO-Y197 | 1.1 |
| GO-Y199 | 1.4 |

As indicated in Table 9, GO-Y193, GO-Y197, and GO-Y199 had a high cell growth inhibitory activity against the malignant melanoma cell line as compared to curcumin. In addition, GO-Y193, GO-Y197, and GO-Y199 had a higher effect than that of GO-Y022 and GO-Y030.

Figure 12:
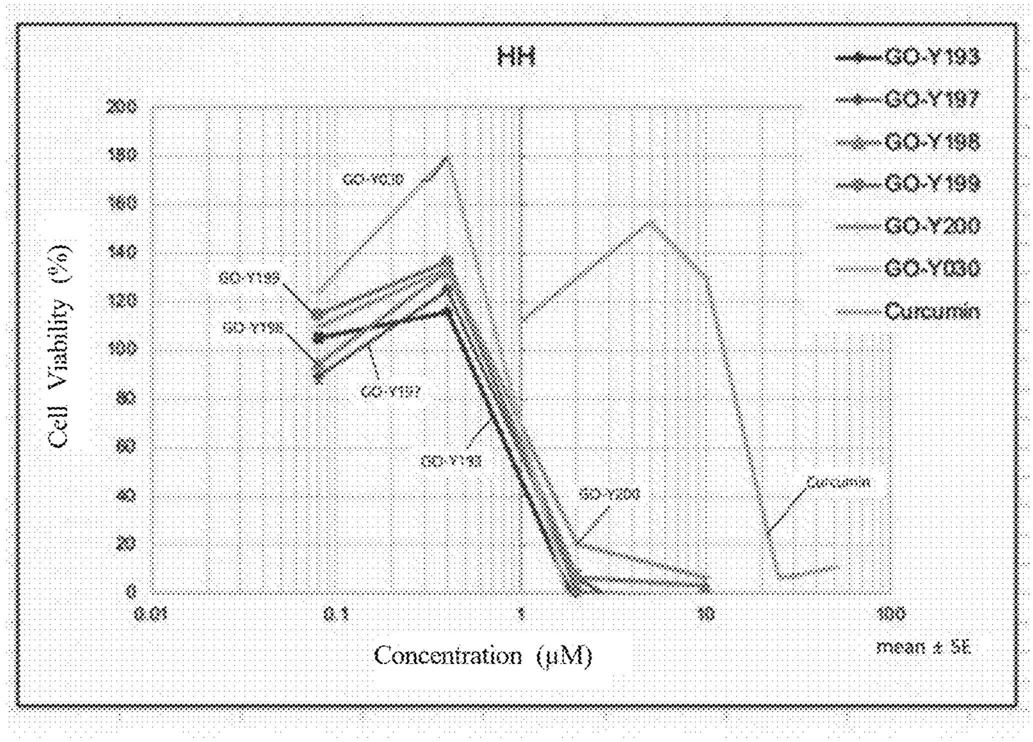
FIG. 12 indicates experimental results of a cell growth inhibitory activity ($IC_{50}$) of various compounds against cutaneous T-cell lymphoma cell lines HH and HUT78.
Figure 12:
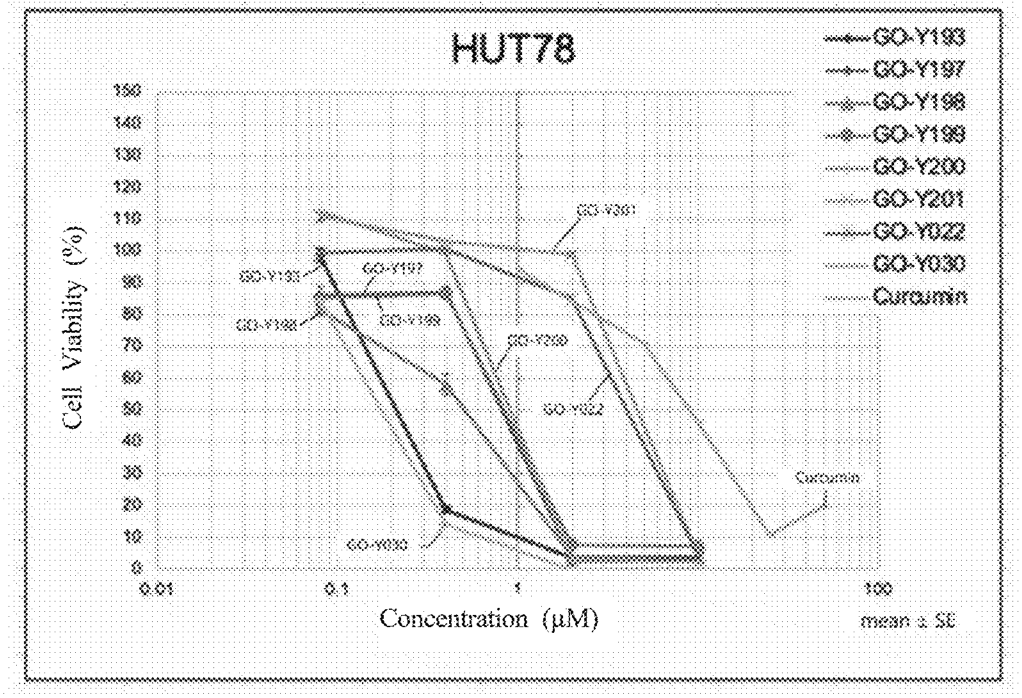

The cell growth inhibitory activity ($IC_{50}$) of each of curcumin, GO-Y022, GO-Y030, GO-Y193, GO-Y197, GO-Y198, GO-Y199, and GO-Y200 against the cutaneous T-cell lymphoma cell lines HH and HUT78 was measured. The method is as described above. The results are indicated in Table 10. FIG. 12 indicates the results of the cell growth inhibitory activity of these compounds against various cancer cell lines.

TABLE 10

| | $IC_{50}$ (μm) | |
|---|---|---|
| | HH | HUT78 |
| Curcumin | 18.05 | 9.01 |
| GO-Y022 | 9.16 | 4.03 |
| GO-Y030 | 1.16 | 0.18 |
| GO-Y193 | 0.96 | 0.21 |
| GO-Y197 | 1.11 | 0.81 |
| GO-Y198 | 1.15 | 0.51 |
| GO-Y199 | 1.11 | 0.84 |
| GO-Y200 | 1.31 | 0.91 |

As indicated in Table 10, GO-Y193, GO-Y197, GO-Y198, GO-Y199, and GO-Y200 had a high cell growth inhibitory activity against any of the cutaneous T-cell lymphoma cell lines as compared to curcumin. In addition, GO-Y193, GO-Y197, GO-Y198, GO-Y199, and GO-Y200 had a higher effect than that of GO-Y022.

[Cytocidal Effect]

The cytocidal effect of GO-Y199 was investigated. The method is as follows. Each cell line was added to 6-well plate by $5\times10^4$, 2 μM and 5 μM of GO-Y199 were added after 24 hours, and the number of cells was counted after 48 hours and 72 hours. The results are indicated in FIG. 13.

Figure 13:
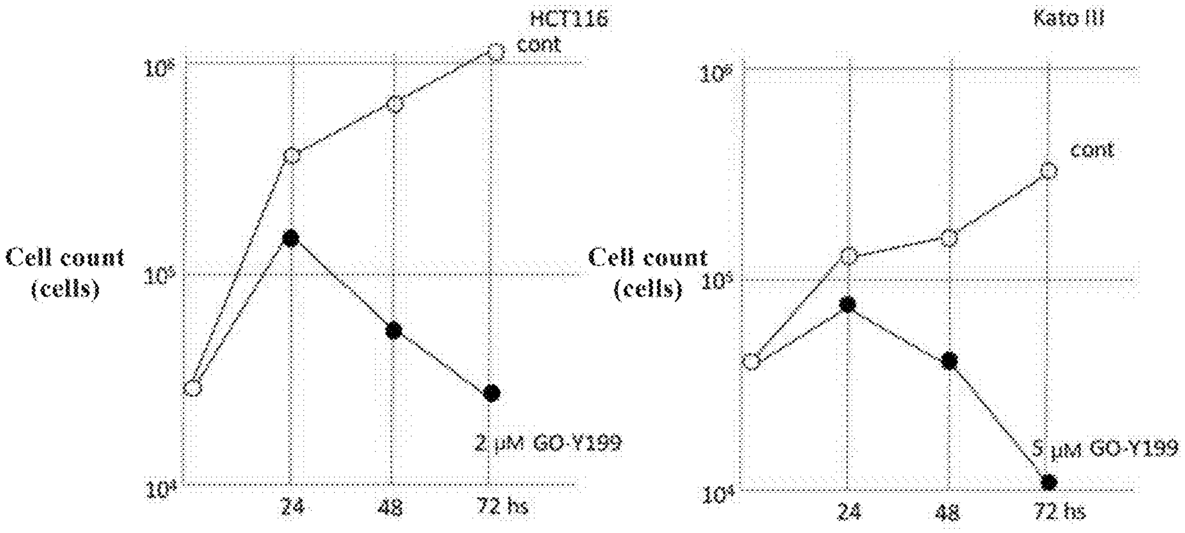
FIG. 13 indicates experimental results of a cytocidal effect of GO-Y199 on HCT116 and Kato III.

As indicated in FIG. 13, GO-Y199 was found to have a cytocidal effect on any of the cancer lines HCT116 and Kato III.

[Influence on NF-kB]

Figure 14:
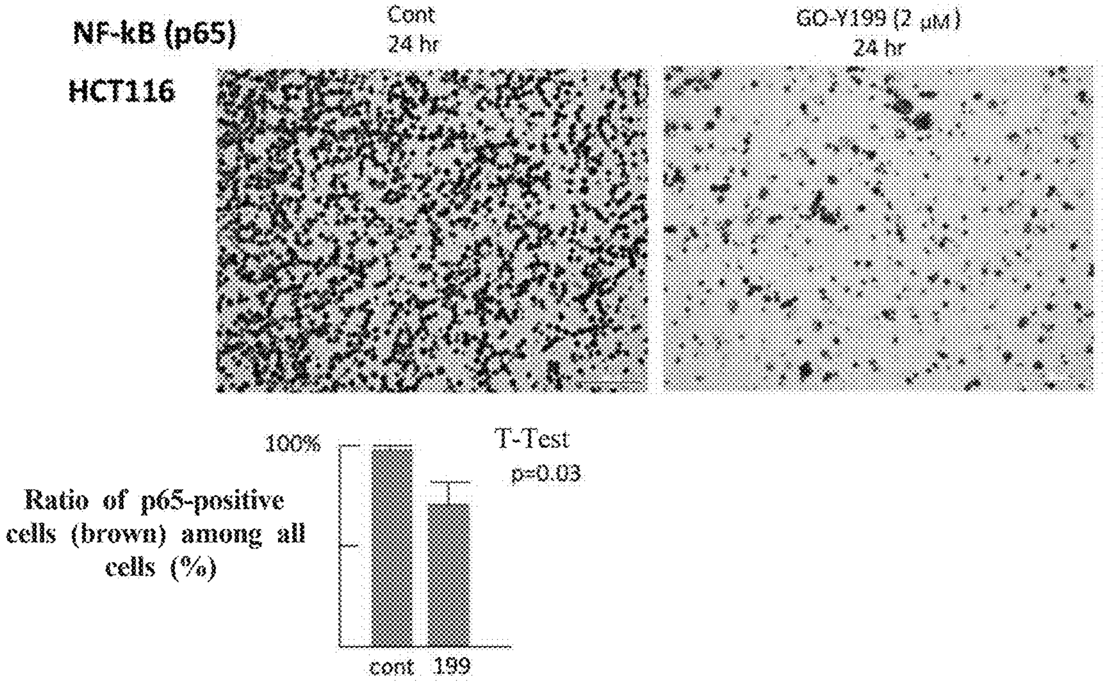
FIG. 14 indicates experimental results of an effect of GO-Y199 on NF-kB.
Figure 15:
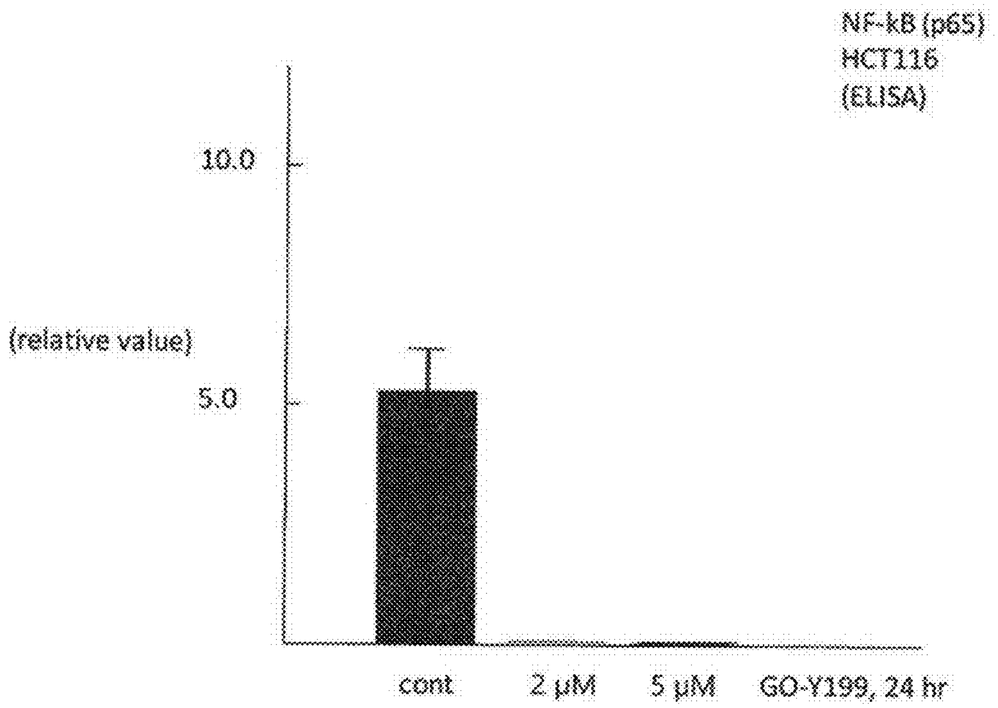
FIG. 15 indicates a comparison result of an NF-kB inhibitory effect of a GO-Y199-added group with respect to a control group.

The influence of GO-Y199 on NF-kB (p65) was investigated. The method is as follows. $3\times10^6$ cells of the HCT116 cell line were added to a 10-cm plate, 2 μM of GO-Y199 was added after 24 hours, the cells were collected after 24 hours, embedded in iPGell (GenOStaff), and fixed in formalin, paraffin blocks were then prepared, and immuno-histochemistry was performed with an anti-NF-kB (p65) antibody. In addition, 2 μM and 5 μM of GO-Y199 were added, lysates were collected after 24 hours, and an expression level of NF-kB (p65) was analyzed using an ELISA-plate (NF-kBp65 (pS536) SimpleStep-ELISA-kit, Abcam). An amount of protein was corrected by the absorbance of A 280 nm. The results are indicated in FIGS. 14 and 15. The upper part of FIG. 14 indicates photographs of the control group and the GO-Y199 (2 μM)-added group after 24 hours. The lower part of FIG. 14 indicates results of the t-test of these groups after 24 hours. FIG. 15 indicates the comparison results of the NF-kB inhibitory effect of GO-Y199 (2 μM, 5 μM)-added groups with respect to the control group.

As indicated in FIG. 14, the proportion of cells expressing NF-kB (p65) in the control group was 96.8±1.1%, while that in the GO-Y199-added group was 69.4±12.4%. As indicated in FIG. 15, the relative expression level of NF-kB (p65) in the control group was 5.27±0.95, while that in the GO-Y199-added groups (2 μM and 5 μM) was 0 and 0, respectively. Thus, it was confirmed that GO-Y199 has an NF-kB inhibitory effect.

[Influence on pSTAT3]

Figure 16:
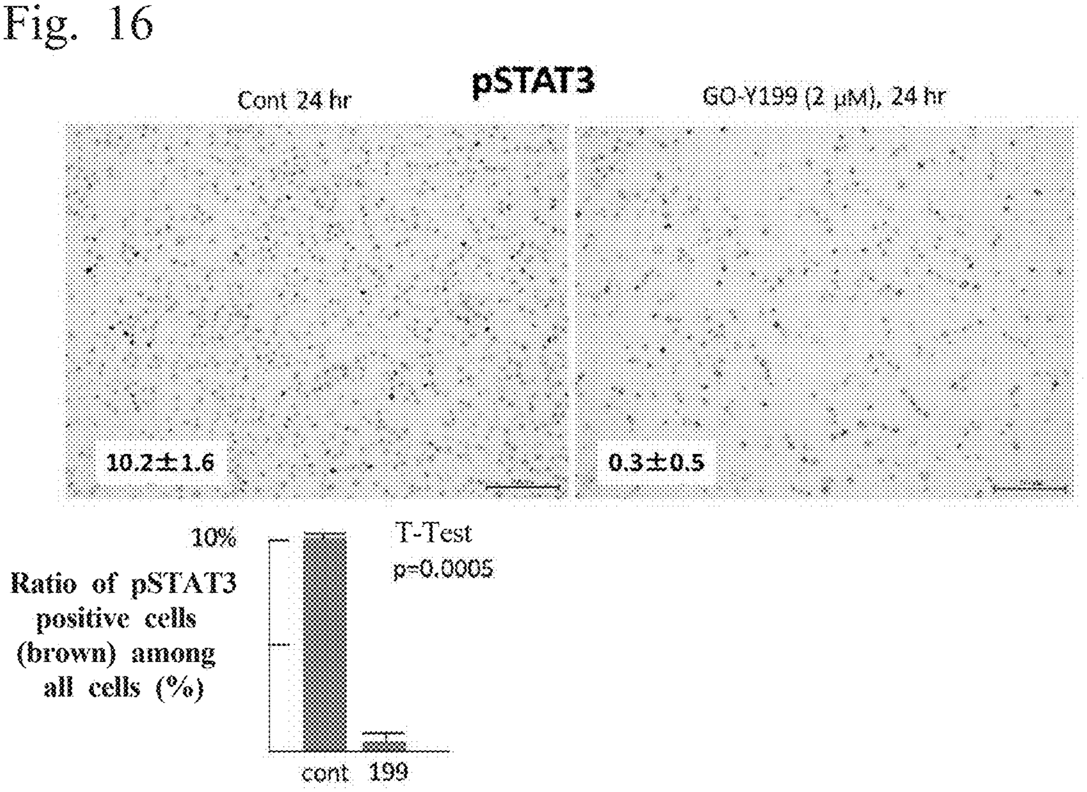
FIG. 16 indicates experimental results of an influence of GO-Y199 on pSTAT3.

The influence of GO-Y199 on pSTAT3 was investigated. The method is as described above. Immunohistochemistry was performed with an anti-pSTAT3 antibody. The results are indicated in FIG. 16. The upper part of FIG. 16 indicates photographs of the control group and the GO-Y199 (2 μM)-added group after 24 hours. The lower part of FIG. 16 indicates results of the t-test of these groups after 24 hours.

As indicated in FIG. 16, the relative expression level of pSTAT3 in the control group was 10.2±1.6%, whereas the relative expression level of pSTAT3 in the GO-Y199 (2 μM)-added group was 0.3±0.5%. Thus, the expression level of pSTAT3 was significantly decreased by the addition of GO-Y199, and it was confirmed that GO-Y199 inhibited the expression of pSTAT3.

[Influence on β-Catenin]

Figure 17:
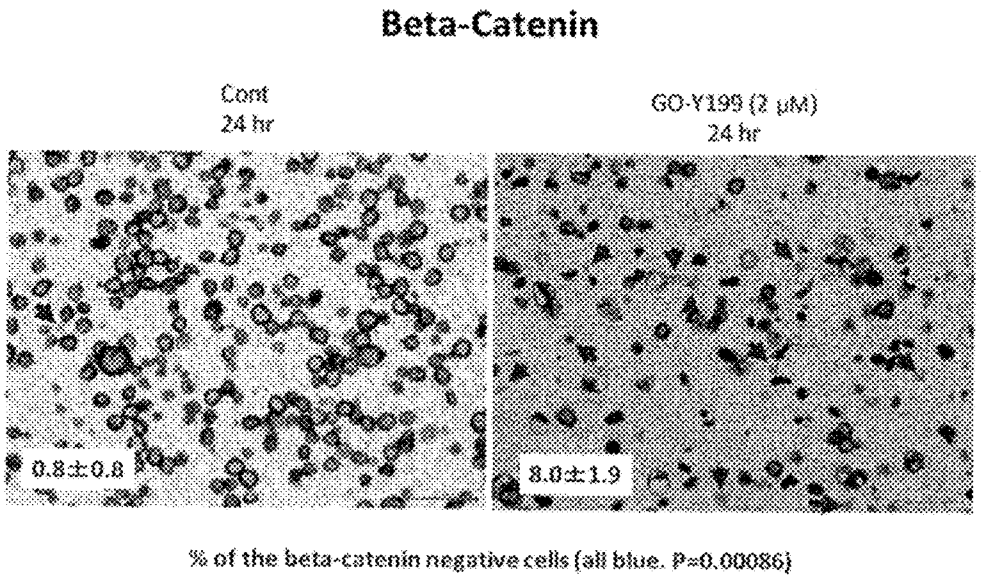
FIG. 17 indicates experimental results of an influence of GO-Y199 on β-catenin.
Figure 18:
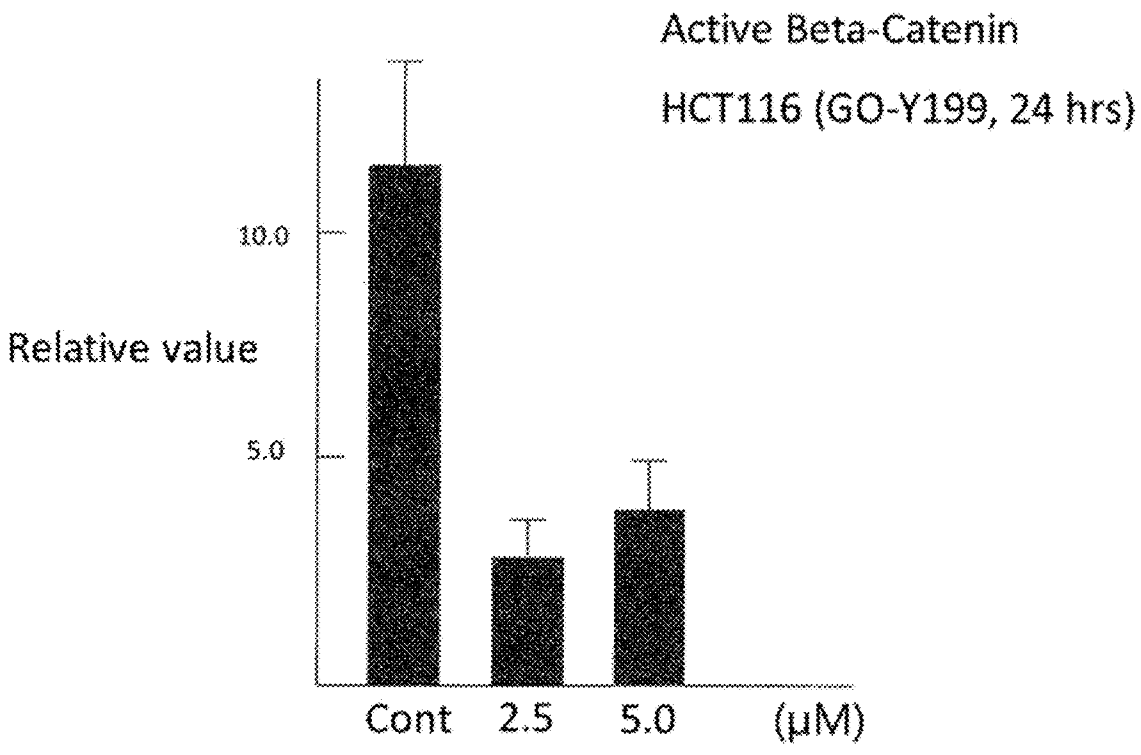
FIG. 18 indicates a comparison result of a β-catenin inhibitory effect of the GO-Y199-added group with respect to the control group.

The influence of GO-Y199 on β-catenin was investigated. The method is as described above. Immunohistochemistry was performed with an anti-β-catenin antibody. Protein quantification was performed using an ELISA plate (proteintech). The results are indicated in FIGS. 17 and 18. FIG. 17 indicates photographs of the control group and the GO-Y199 (2 μM)-added group after 24 hours. The numerical values in FIG. 17 are the results of the t-test of β-catenin inactivated cells. FIG. 18 indicates the comparison results of the β-catenin inhibitory effect of GO-Y199 (2 μM, 5 μM)-added groups with respect to the control group.

As indicated in FIG. 18, the relative expression level of β-catenin was 11.5±2.3 in the control group, while it was 2.8±0.8 in the GO-Y199 (2 μM)-added group and 3.9±1.1 in the GO-Y199 (5 μM)-added group, indicating that the addition of GO-Y199 significantly reduced the expression level of β-catenin. Accordingly, it was confirmed that GO-Y199 has an β-catenin inhibitory effect.

[Influence on Fatty Acid Synthetase]

Figure 19:
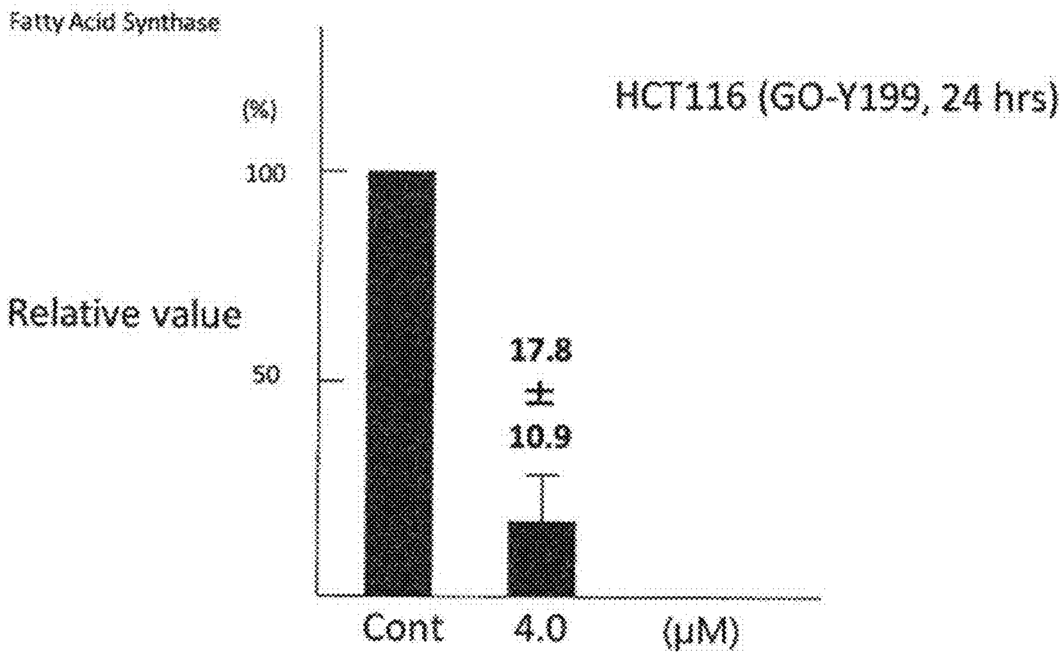
FIG. 19 indicates a comparison result of a fatty acid synthetase inhibitory effect of the GO-Y199-added group with respect to the control group.

The influence of GO-Y199 on fatty acid synthetase was investigated. The method is as described above. Protein quantification was performed using a Human Fatty acid synthase ELISA Kit (MyBioSource). The results are indicated in FIG. 19. FIG. 19 indicates the comparison result of the fatty acid synthetase inhibitory effect of the GO-Y199 (4 μM)-added group with respect to the control group.

As indicated in FIG. 19, it was confirmed that GO-Y199 has a significant fatty acid synthetase inhibitory effect.

[Influence on Caspase 3]

Figure 20:
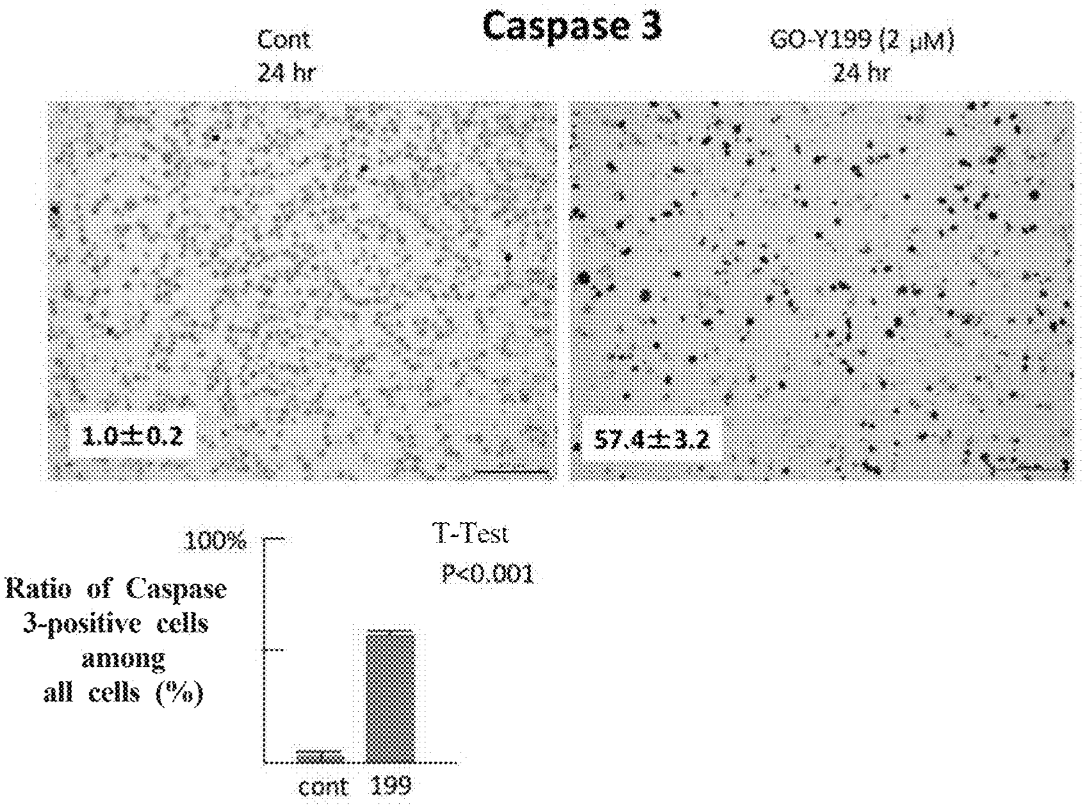
FIG. 20 indicates experimental results of an influence of GO-Y199 on caspase 3.
Figure 21:
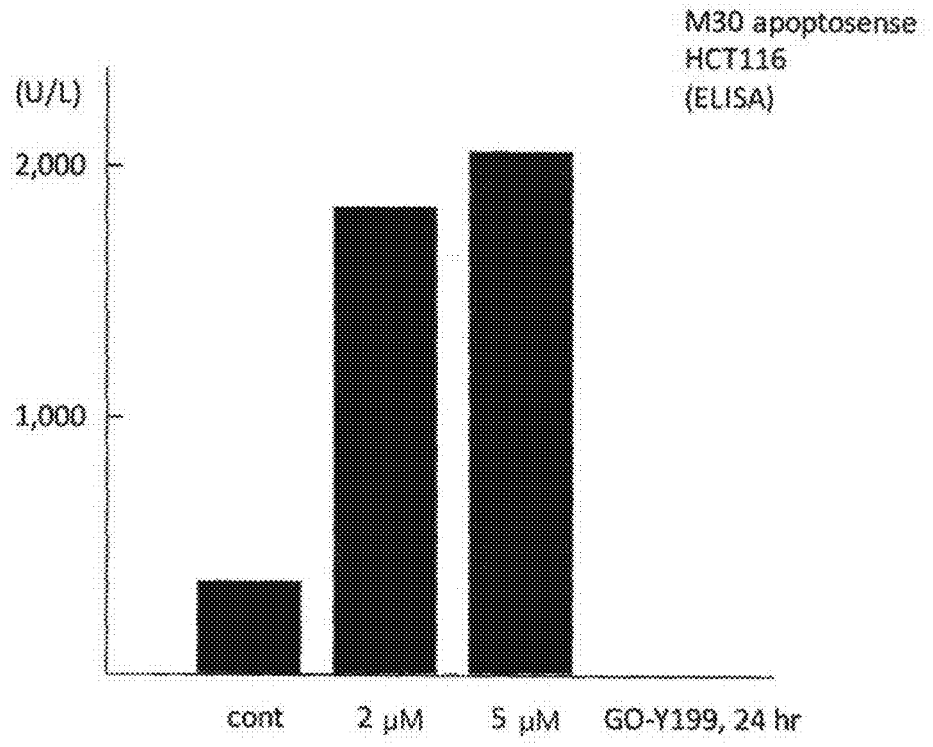
FIG. 21 indicates a comparison result of an influence of the GO-Y199-added group on apoptosis with respect to the control group.

The influence of GO-Y199 on Caspase 3 was investigated. The method is as described above. Immunohistochemistry was performed with an anti-Caspase 3 antibody. Quantification of apoptosis-related protein was performed using M30 Apotosense ELISA (PEVIVA). The results are indicated in FIGS. 20 and 21. The upper part of FIG. 20 indicates photographs of the control group and the GO-Y199 (2 μM)-added group after 24 hours. The lower part of FIG. 20 indicates the percentages of Caspase 3-expressing cells after 24 hours. FIG. 21 indicates induction of apoptosis-related protein in the GO-Y199 (2 μM, 5 μM)-added groups with respect to the control group.

As indicated in FIG. 20, the proportion of Caspase 3-expressing cells in the control group was 1.0±0.1%, while the proportion in the GO-Y199 (2 μM)-added group was 57.4±2.6%, which significantly increased. In addition, as indicated in FIG. 21, while the activity was 360 U/L in the control group, the activity was 1,830 U/L in the GO-Y199 (2 μM)-added group and 2,050 U/L in the GO-Y199 (5 μM)-added group, indicating that the addition of GO-Y199 induced apoptosis-related protein. Accordingly, it was confirmed that GO-Y199 activates caspase 3 to induce apoptosis.

[Angiogenesis Inhibitory Activity]

Figure 22:
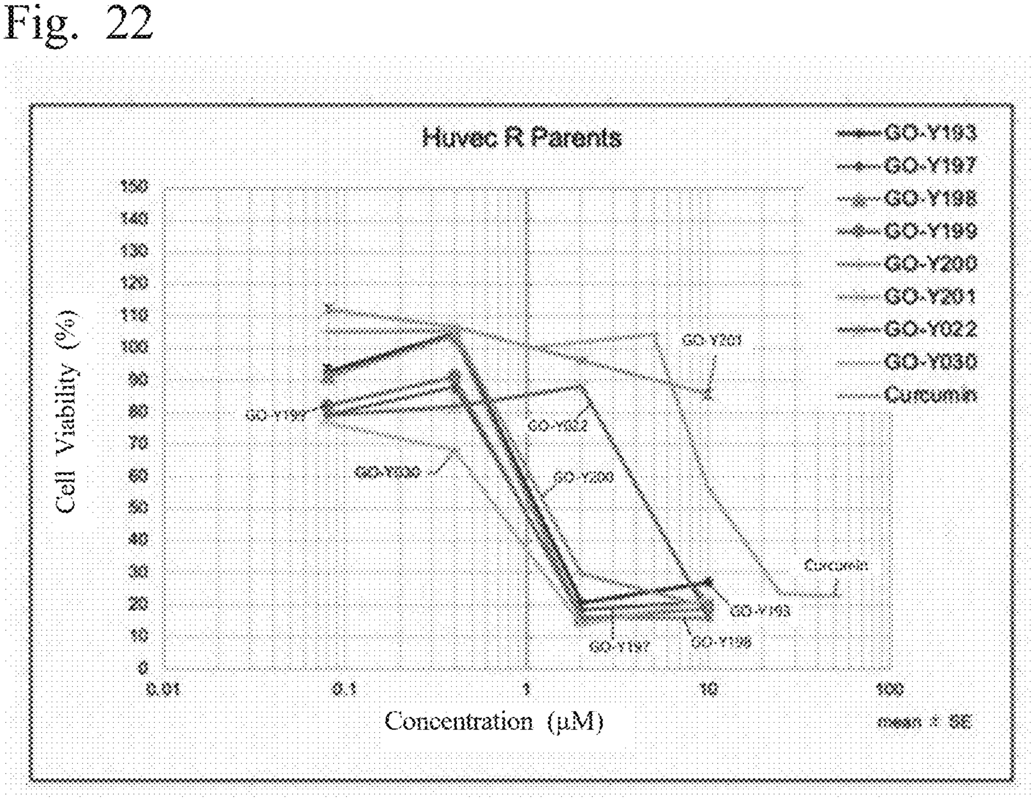
FIG. 22 indicates experimental results of an angiogenesis inhibitory activity of various compounds on vascular endothelial cells HUVEC-R.

The angiogenesis inhibitory activity of each of curcumin, GO-Y022, GO-Y030, GO-Y193, GO-Y197, GO-Y198, GO-Y199, and GO-Y200 on vascular endothelial cells HUVEC-R resistant to an angiogenesis-inhibiting agent Ki8751 was investigated. HUVEC-R was cultured in the presence of each compound using an EGMTM-2 Bullet Kit (Takara Bio Inc., Otsu, Japan), and the number of cells was measured after 72 hours. In addition, $IC_{50}$ was determined from the results. GO-Y030 is known to have an angiogenesis inhibitory activity, with which comparison was made. The results are indicated in Table 11 and FIG. 22.

TABLE 11

| | $IC_{50}$ (μm) HUVEC-R |
|---|---|
| GO-Y193 | 1.14 (1.65) |
| GQ-Y197 | 0.96 (1.39) |
| GQ-Y198 | 1.08 (1.57) |
| GO-Y199 | 0.96 (1.39) |
| GO-Y200 | 1.3 (1.88) |
| Curcumin | 11.9 (17.2) |
| GO-Y030 | 0.69 (1.00) |
| GO-Y022 | 4.7 (6.81) |

From Table 11, GO-Y193, GO-Y197, GO-Y198, GO-Y199, and GO-Y200 had a high angiogenesis inhibitory activity as compared with curcumin. In addition, GGO-Y193, GO-Y197, GO-Y198, GO-Y199, and GO-Y200 had a higher effect than that of GO-Y022.

[Regulatory T Cell Inhibitory Activity]

Figure 23:
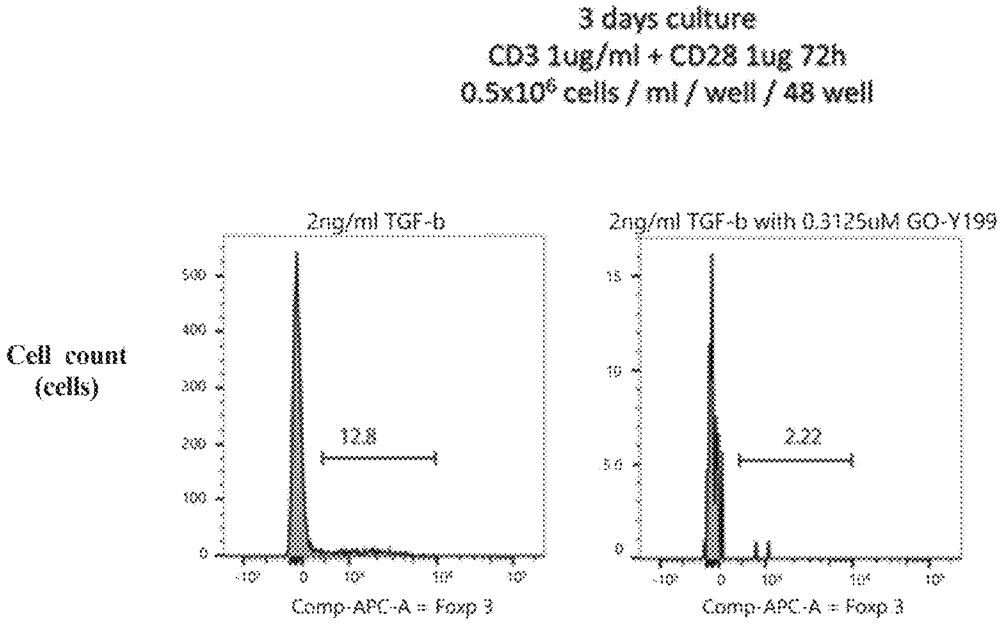
FIG. 23 indicates experimental results of a regulatory T-cell suppressive activity of GO-Y199.

Naive $CD4^+$ T cells were collected from the spleen of a mouse using a $CD4^+CD62L^{hi}$ T Cell Isolation Kit (Miltenyi Biotec). $0.5\times10^6$ cells/mL of the collected T cells were added to a RPMI 1640 medium to which penicillin/streptomycin (5,000 units/mL), 10% fetal bovine serum, and 50 μM of 2-mercaptoethanol were added. Subsequently, 1 μg/mL of anti-CD3 antibody (eBioscience) was added to the medium, and 1 μg/ml of anti-CD28 antibody (eBioscience) was further added thereto. The medium was then cultured at 37° C. for 3 days. Then, TGF-β1 (2 ng/mL) was added to the medium and cultured for 24 hours. After that, a FOXP3 Staining Buffer Kit (eBioscience) was used to fix the cells and treat cell membranes, and FOXP3 in the nuclei was stained. The stained cells were measured using a BD LSR-Fortessa™ (BD Bioscience) flow cytometer, and the obtained data was analyzed with FlowJo (Tree-Star version). The results are indicated in FIG. 23.

An induction ratio of FOXP3-positive regulatory T cells as a control group was 12.8%, while the induction ratio of regulatory T cells to which 0.3 μM of GO-Y199 was added was suppressed to 2.22%.

[In Vivo Antitumor Effect]

The in vivo antitumor effect of GO-Y199 was investigated. The method is as follows. HCT116 was implanted subcutaneously into a nude mouse. After tumor formation, 100 mM GO-Y199 in DMSO was dissolved in 100 μL of PBS and injected once into the tail vein of the mouse (corresponding to 1 mg of GO-Y199). As a control group, a DMSO-PBS solution having the equivalent concentration was injected once into the tail vein. The maximum diameter of the tumor was measured 4 days after the administration. The results are indicated in FIG. 24.

Figure 24:
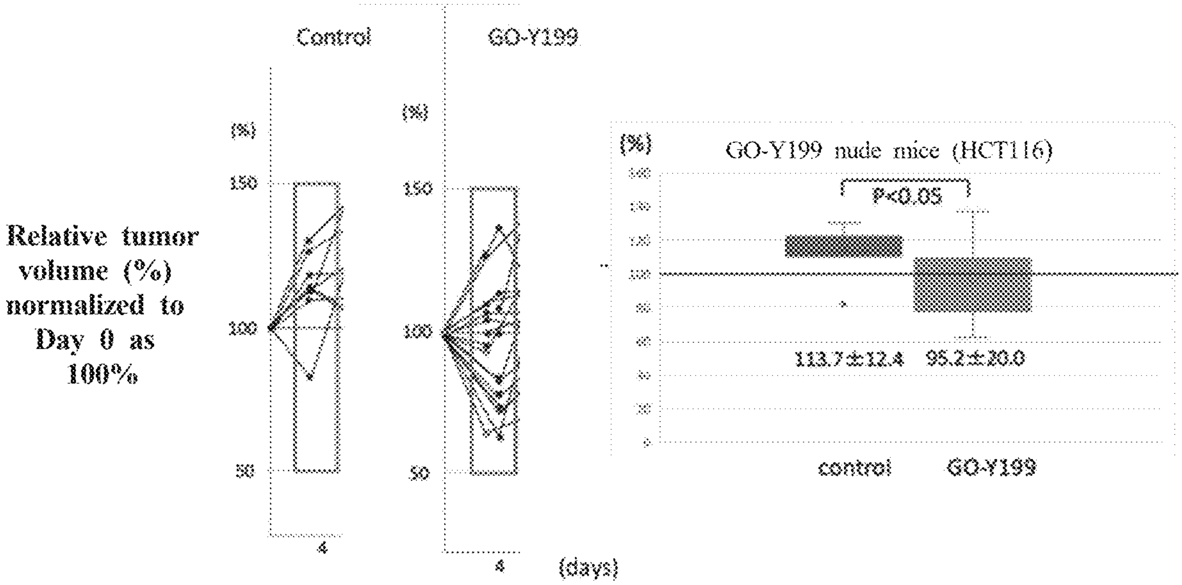
FIG. 24 indicates experimental results of an in vivo antitumor effect of GO-Y199.

FIG. 24 indicates the relative degree of tumor augmentation between the control group (left) and the GO-Y199 intravenous injection group (right). While the tumor augmentation of the control group was 113.7±12.4% of that before the administration, the tumor augmentation of the GO-Y199 intravenous injection group was 95.2±20.0% of that before the administration, indicating that the addition of GO-Y199 significantly suppressed the tumor augmentation. Accordingly, it was confirmed that GO-Y199 also exhibited an antitumor activity in vivo.

Figure 25:
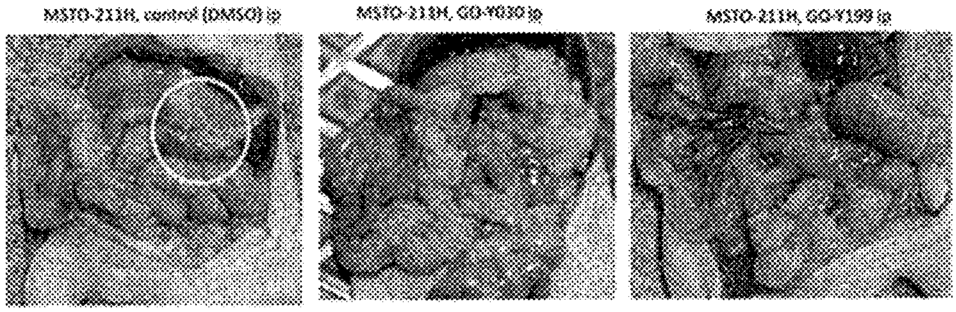
FIG. 25 indicates experimental results of an antitumor effect of GO-Y199 on malignant mesothelioma cells using an animal model.
Figure 25:
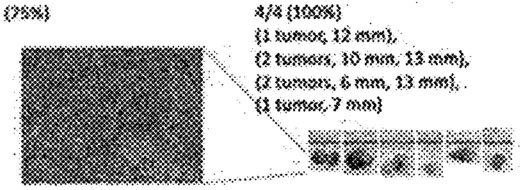

An animal model was used to investigate the antitumor effect of GO-Y199 on malignant mesothelioma cells. The method is as follows. $2.8\times10^6$ MSTO-211H cells were intraperitoneally transplanted into each of 5 nude mice. From Day 5, 43 μL of 100 mM GO-Y199 in DMSO was diluted to 500 μL with PBS and intraperitoneally administered to the mice (equivalent to 5 mg of GO-Y199). As a control group, a DMSO-PBS solution having the equivalent concentration was intraperitoneally administered to each of four nude mice to which MSTO-211H cells were intraperitoneally transplanted in the same manner. The administration was performed 5 times in total at intervals of 5 days. After 30 days, the mice were sacrificed, necropsied, and analyzed. The results are indicated in FIG. 25.

Figure 26:
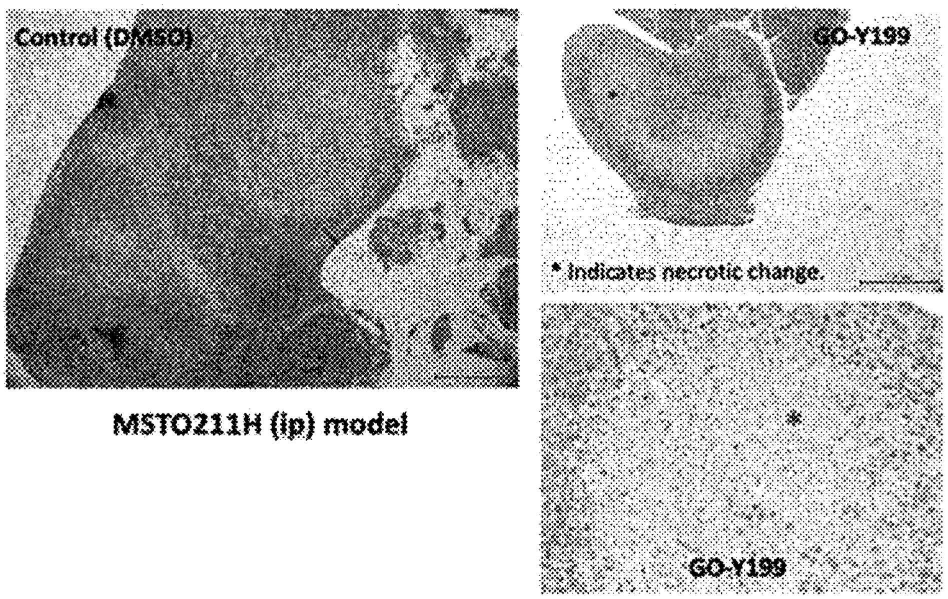
FIG. 26 indicates photographs showing a result of pathologic analysis of malignant mesothelioma cells.

In one animal in the GO-Y199 administration group, tumor formation was observed at the puncture site at which MSTO-211H cells were intraperitoneally administered. Tumor formation was not observed in the control group. Microscopic peritoneal disseminated lesions were observed in 4 animals (80%) in the GO-Y199 administration group and 3 animals (75%) in the control group. On the other hand, one disseminated nodule having a maximum diameter exceeding 5 mm was observed in one animal (20%) in the GO-Y199 administration group, while a total of six disseminated nodules were observed in four animals (100%) in the control group. In addition, the size (maximum diameter) was 5 mm in the GO-Y199 administration group, while it was 6 to 13 mm (average 10.2 mm) in the control group, which was large. As indicated in FIG. 26, according to pathologic analysis, the inside of the disseminated nodule of the GO-Y199 administration group was necrotic, while it was filled with tumor cells in the control group.

[Blood Concentration After Intravenous Injection]

Figure 27:
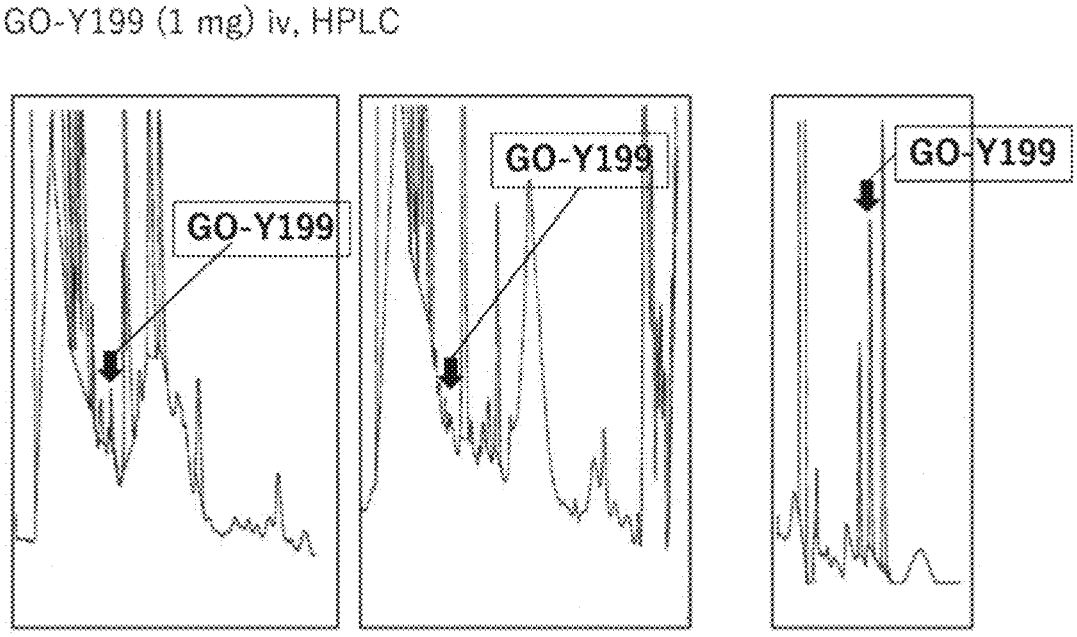
FIG. 27 indicates a result of HPLC analysis of blood after intravenous injection.
Figure 28:
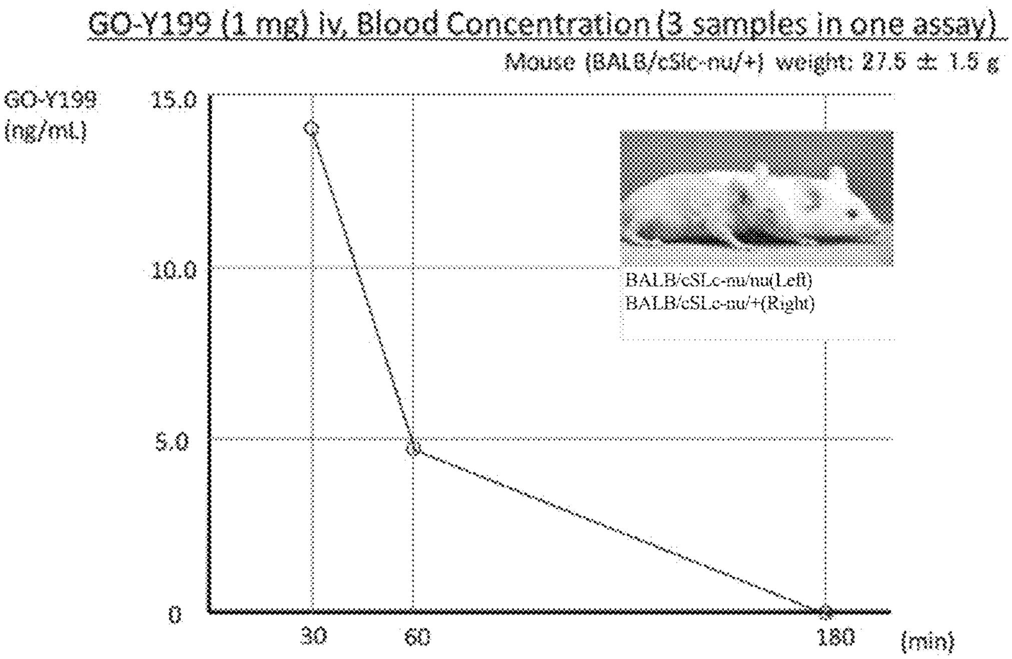
FIG. 28 indicates a change over time in blood concentration of GO-Y199 after intravenous injection.

The blood concentration of GO-Y199 after intravenous injection was investigated. The method is as follows. To BALB/cSlc-nu/+ mice, the equivalent of 1 mg of GO-Y199 was injected into the tail vein as described above, blood was collected from the orbital vein over time, and the serum was subjected to HPLC to measure the blood concentration of GO-Y199. The results are indicated in FIGS. 27 and 28. FIG. 27 indicates results of HPLC analysis of blood after intravenous injection. FIG. 28 indicates results of changes over time in the blood concentration of GO-Y199 after intravenous injection.

FIG. 27 indicates raw data of the HPLC analysis. As indicated in FIG. 28, the blood concentration of GO-Y199 rapidly decreased until 60 minutes after intravenous injection, and then gently decreased, and GO-Y199 disappeared from the blood 180 minutes after the intravenous injection. From this, it was confirmed that GO-Y199 can be intravenously administered, the blood concentration is maintained for 3 hours after the administration, and thereafter, is rapidly metabolized and excreted.

[Safety and Toxicity Test]

Figure 29:
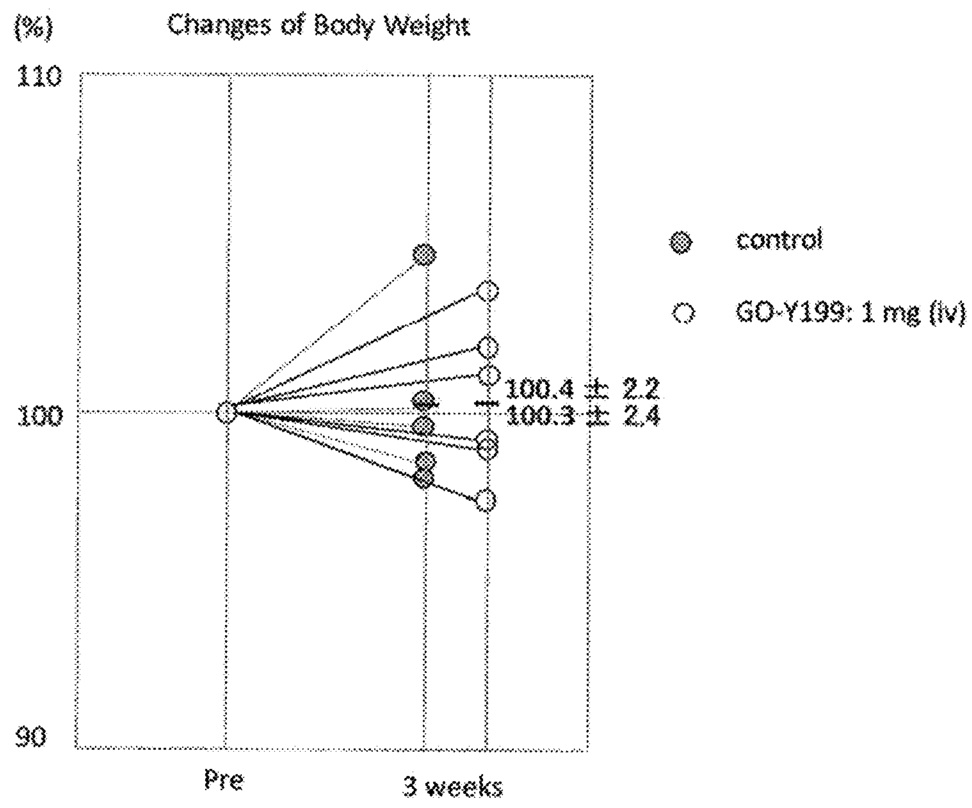
FIG. 29 indicates changes in body weight of mice after intravenous injection.
Figure 30:
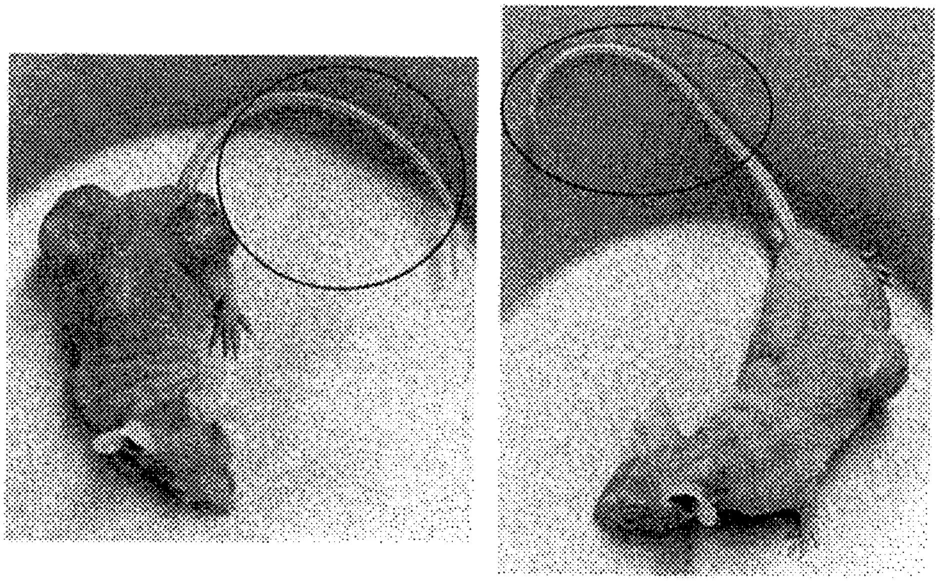
FIG. 30 indicates photographs of tails of mice after intravenous injection.

In vivo safety and toxicity of GO-Y199 were investigated. The method is as follows. As described above, the equivalent of 1 mg of GO-Y199 was injected into the tail vein, blood was collected from the orbital vein 7 days later, and a hemoglobin value (Hb), the number of white blood cells (WBC), and the number of platelets (Plt) were measured with Cell tac MEK-5258 (available from Nihon Kohden Corporation). A creatinine value (Cre), a total bilirubin value (T-Bil), and an AST value were subjected to outsourcing (measured in Skylight Biotech Inc.). The results are indicated in Tables 12 and 13. FIG. 29 indicates change in body weight of mice after intravenous injection. FIG. 30 indicates photographs of the tail of the mouse after intravenous injection.

TABLE 12

At Day 7 (Single, 1 mg/body, tail vein iv, control: 10% DMSO, 100 μL)

| Hematology | Control | GO-Y199, Iv, single |
|---|---|---|
| Hb (g/dL) | 14.2, 15.6 | 14.9. 15.8 |
| WBC (/μL) | 6500, 13900 | 6400, 69700 |
| Plt (104/μL) | 79.1, 107.0 | 87.7, 78.3 |

TABLE 13

| Samples | Cre (mg/dl) | T-Bil (mg/dl) | AST (U/L) |
|---|---|---|---|
| Control-1 | 0.45 | 0.7 | 75 |
| Control-2 | 0.14 | 0.4 | 53 |
| Control-3 | 0.14 | 0.3 | 67 |
| Ave. ± SD | 0.24 ± 0.15 | 0.47 ± 0.17 | 65.0 ± 9.1 |
| GO-Y199-1 | 0.14 | 0.6 | 72 |
| GO-Y199-2 | 0.13 | 0.2 | 51 |
| GO-Y199-3 | 0.18 | 0.2 | 63 |
| Ave. ± SD | 0.15 ± 0.02 | 0.33 ± 0.19 | 62.0 ± 8.6 |

As indicated in Tables 12 and 13, no significant difference was confirmed between the control group and the GO-Y199 intravenous injection group. As indicated in FIG. 29, there was no difference in body weight between the two groups. As indicated in FIG. 30, no local abnormal finding was observed in the tails of all intravenously injected mice. From the above results, it was confirmed that GO-Y199 is safe for the mouse model.

The invention claimed is:

1. A compound represented by the following general formula or a salt thereof:

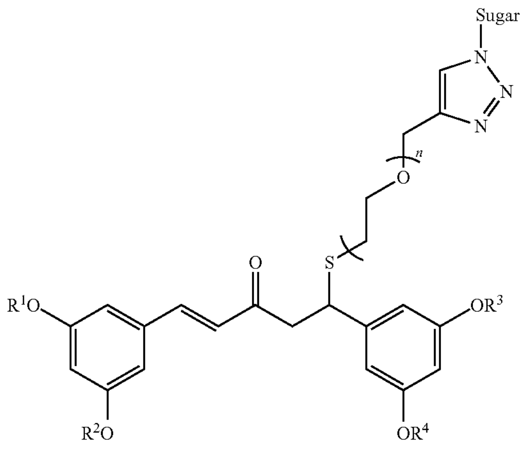

wherein $R^1$ to $R^4$ are substituents selected from a hydrogen atom, a $C_{1-4}$ lower alkyl group, a hydroxy $C_{1-4}$ lower alkyl group, a $C_{1-4}$ lower alkoxy $C_{1-4}$ lower alkyl group, and a $C_{1-4}$ lower alkoxy $C_{1-4}$ lower alkoxy $C_{1-4}$ lower alkyl group, and $R^1$ to $R^4$ may be the same or different, n is 1 to 6, and Sugar is a monosaccharide or a disaccharide.

2. The compound according to claim 1, or a salt thereof, wherein the sugar is D-galactose, L-glucose, D-mannose, D-lactose, or D-maltose.

3. The compound according to claim 1, or a salt thereof, wherein the sugar is D-mannose, D-lactose, or D-maltose.

* * * * *